United States Patent [19]

Häbich et al.

[11] Patent Number: 5,529,998
[45] Date of Patent: Jun. 25, 1996

[54] BENZOXAZOLYL- AND BENZOTHIAZOLYLOXAZOLIDINONES

[75] Inventors: Dieter Häbich; Bernd Riedl; Martin Ruppelt; Andreas Stolle, all of Wuppertal, Germany; Hanno Wild, Orange, Conn.; Rainer Endermann, Wuppertal, Germany; Klaus D. Bremm, Recklinghausen, Germany; Hein-Peter Kroll, Wuppertal, Germany; Harald Labischinski, Wuppertal, Germany; Klaus Schaller, Wuppertal, Germany; Hans-Otto Werling, Wuppertal, Germany

[73] Assignee: Bayer Aktiengesellschaft, Leverkusen, Germany

[21] Appl. No.: 508,245

[22] Filed: Jul. 27, 1995

[30] Foreign Application Priority Data

Aug. 3, 1994 [DE] Germany .......................... 44 27 475.0
Apr. 18, 1995 [DE] Germany ........................ 195 14 313.2

[51] Int. Cl.$^6$ .................. C07D 413/02; C07D 417/02; A61K 31/425; A61K 31/535
[52] U.S. Cl. .................. 514/233.8; 514/367; 514/375; 540/575; 544/121; 544/315; 544/357; 544/364; 544/368; 546/198; 546/256; 546/187; 546/19; 546/270.1; 546/271.7; 548/147; 548/161; 548/166; 548/169; 548/170; 548/171; 548/178; 548/216; 548/217; 548/221; 548/222; 548/224
[58] Field of Search .......................... 544/121; 548/161, 548/178, 217, 222; 514/233.8

[56] References Cited

U.S. PATENT DOCUMENTS 4,766,132  8/1988  Kay .......................................... 546/332

*Primary Examiner*—Robert W. Ramsuer
*Attorney, Agent, or Firm*—Sprung Horn Kramer & Woods

[57] ABSTRACT

The invention relates to benzoxazolyl- and benzothiazolyloxazolidinones, processes for their preparation and their use as medicaments, in particular as antibacterial medicaments.

6 Claims, No Drawings

BENZOXAZOLYL- AND BENZOTHIAZOLYLOXAZOLIDINONES

The present invention relates to benzoxazolyl- and benzothiazolyloxazolidinones, processes for their preparation and their use as medicaments, in particular as antibacterial medicaments.

N-Aryloxazolidinones having an antibacterial action are known from the publications U.S. Pat. No. 5,254,577, U.S. Pat. No. 4,705,799, EP 311,090, U.S. Pat. No. 4,801,600, U.S. Pat. No. 4,921,869, U.S. Pat. No. 4,965 268, EP 312,000 and C. H. Park et al., J. Med. Chem. 35, 1156 (1992).

Oxazolidinone derivatives having a monoamineoxidase-inhibiting action furthermore are described in PCT 93 08 179 A.

The present invention relates to benzoxazolyl- and benzothiazolyloxazolidinones of the general formula (I)

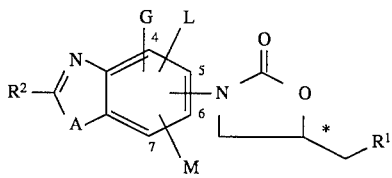

in which

A represents an oxygen atom, or represents a radical of the formula —S(O)$_a$, wherein a denotes the number 0 or 2, $R^1$ represents azido, or represents a group of the formula O—SO$_2$R$^3$ or —NR$^4$R$^5$, wherein $R^3$ denotes straight-chain or branched alkyl having up to 4 carbon atoms, or phenyl which is optionally substituted by straight-chain or branched alkyl having up to 4 carbon atoms, $R^4$ and $R^5$ are identical or different and denote cycloalkyl having 3 to 6 carbon atoms, hydrogen, phenyl or straight-chain or branched alkyl having up to 8 carbon atoms or an amino-protective group, or $R^4$ or $R^5$ denote a group of the formula —CO—R$^6$, wherein $R^6$ denotes cycloalkyl having 3 to 6 carbon atoms, straight-chain or branched alkyl or alkoxy having in each case up to 8 carbon atoms, phenyl or hydrogen, G, L and M are identical or different and represent hydrogen, carboxyl, halogen, cyano, formyl, trifluoromethyl, nitro or straight-chain or branched alkoxy, alkoxycarbonyl, alkylthio or acyl having in each case up to 6 carbon atoms, or represent straight-chain or branched alkyl having up to 6 carbon atoms, which can in turn be substituted by hydroxyl, by straight-chain or branched alkoxy or acyl having up to 5 carbon atoms or by a group of the formula —NR$^7$R$^8$, wherein $R^7$ and $R^8$ are identical or different and denote hydrogen, straight-chain or branched alkyl having up to 4 carbon atoms or phenyl, or together with the nitrogen atom form a 5- to 6-membered saturated heterocyclic ring with optionally a further hetero atom from the series consisting of N, S and/or O, which can in turn optionally be substituted, also on another nitrogen atom, by straight-chain or branched alkyl or acyl having up to 3 carbon atoms, and/or optionally represent a group of the formula —NR$^7$R$^8$', wherein $R^7$' and $R^8$' are identical or different and have the abovementioned meaning of $R^7$ and $R^8$ and are identical to or different from these, and/or optionally represent (C$_2$–C$_8$)-alkenylphenyl, phenyl or a 5- or 6-membered saturated or unsaturated heterocyclic radical having up to 3 hetero atoms from the series consisting of S, N and/or O, each of which is in turn optionally substituted by a group of the formula —CO—NR$^9$R$^{10}$, NR$^{11}$R$^{12}$, NR$^{13}$—SO$_2$—R$^{14}$, R$^{15}$R$^{16}$N—SO$_2$— or R$^{17}$—S(O)$_b$—, wherein b denotes the number 0, 1 or 2, $R^9$, $R^{10}$, $R^{13}$, $R^{15}$ and $R^{16}$ are identical or different and denote hydrogen straight-chain or branched alkyl having up to 6 carbon atoms or phenyl, $R^{11}$ and $R^{12}$ are identical or different and have the abovementioned meaning of $R^7$ and $R^8$ and are identical to or different from these, $R^{14}$ and $R^{17}$ are identical or different and have the abovementioned meaning of $R^3$ and are identical to or different from this, and/or are in turn optionally substituted up to twice in an identical or different manner by carboxyl, halogen, cyano, formyl, trifluoromethyl, nitro, phenyl, straight-chain or branched alkoxy, alkoxycarbonyl, alkylthio or acyl having in each case up to 6 carbon atoms or by straight-chain or branched alkyl having up to 6 carbon atoms, which can in turn by substituted by hydroxyl, by straight-chain or branched alkoxy or acyl having up to 5 carbon atoms or by a group of the formula —NR$^{18}$R$^{19}$, wherein $R^{18}$ and $R^{19}$ have the abovementioned meaning of $R^7$ and $R^8$ and are identical to or different from these, $R^2$ represents hydrogen, formyl or carboxyl, or represents straight-chain or branched alkoxycarbonyl having up to 6 carbon atoms, or represents straight-chain or branched alkyl or alkenyl having in each case up to 8 carbon atoms, each of which is optionally substituted by hydroxyl, halogen or by straight-chain or branched alkoxy, acyl, alkylthio or alkoxycarbonyl having in each case up to 6 carbon atoms or phenyl, which can in turn be substituted by halogen, or represents aryl having 6 to 10 carbon atoms, which is optionally substituted by carboxyl, halogen, cyano, formyl, trifluoromethyl, nitro, straight-chain or branched alkoxy, alkoxycarbonyl, alkylthio or acyl having in each case up to 6 carbon atoms or by straight-chain or branched alkyl having up to 6 carbon atoms, or represents a radical of the formula —NR$^{20}$R$^{21}$, —OR$^{22}$ or —S(O)$_c$—R$^{23}$, wherein $R^{20}$ denotes cycloalkyl having 3 to 6 carbon atoms, phenyl, straight-chain or branched acyl having up to 6 carbon atoms or straight-chain or branched alkyl having up to 8 carbon atoms, which is optionally substituted by hydroxyl, straight-chain or branched alkoxy or hydroxy-substituted alkoxy having in each case up to 6 carbon atoms, by a 5- to 6-membered aromatic heterocyclic radical having up to 3 hetero atoms from the series consisting of S, N and/or O, or by phenyl, which can in turn be substituted by hydroxyl, trifluoromethyl, halogen, nitro or by straight-chain or branched alkoxy having up to 4 carbon atoms, or alkyl is optionally substituted by a radical of the formula —NR$^{24}$R$^{25}$ or $$\underset{O}{\overset{O}{\diagdown}}\hspace{-1em}\diagup$$

wherein $R^{24}$ and $R^{25}$ are identical or different and denote hydrogen or straight-chain or branched alkyl having up to 4 carbon atoms, or $R^{20}$ denotes a radical of the formula $$\underset{R^{27}-CH-}{\overset{O\diagdown\hspace{-0.3em}\diagup C-R^{26}}{|}}$$

wherein $R^{26}$ denotes hydroxyl, straight-chain or branched alkoxy having up to 4 carbon atoms or a radical of the formula —$NR^{28}R^{29}$, wherein $R^{28}$ and $R^{29}$ denote hydrogen or straight-chain or branched alkyl having up to 5 carbon atoms, cycloalkyl having 3 to 6 carbon atoms or phenyl, $R^{27}$ denotes hydrogen or straight-chain or branched alkyl having up to 7 carbon atoms, which is optionally substituted by indolyl, hydroxyl, mercaptyl, imidazolyl, methylthio, amino, phenyl, hydroxy-substituted phenyl or by a radical of the formula —CO—$NH_2$, —$CO_2H$ or $$\underset{NH_2}{\overset{HN=C-,}{|}}$$

or $R^{20}$ denotes a radical of the formula $$T\diagup\hspace{-0.3em}\diagdown N-(CH_2)d-$$

wherein d denotes the number 0, 1, 2, 3, 4, 5 or 6,

T denotes an oxygen atom or a group of the formula $CH_2$ or —$NR^{30}$, wherein $R^{30}$ denotes hydrogen, phenyl or straight-chain or branched alkyl having up to 6 carbon atoms, which is optionally substituted by hydroxyl, and $R^{21}$ has the abovementioned meaning of $R^{20}$ and is identical to or different from this, or denotes hydrogen, $R^{22}$ denotes straight-chain or branched alkyl having up to 8 carbon atoms, which is optionally substituted by straight-chain or branched alkoxy or hydroxy- or alkoxy-substituted alkoxy having in each case up to 6 carbon atoms, cycloalkyl having 3 to 6 carbon atoms or a 6-membered aromatic, optionally benzo-fused heterocyclic radical having up to 3 nitrogen atoms, which can in turn be substituted up to twice in an identical or different manner by nitro, trifluoromethyl, halogen, cyano, hydroxyl or by straight-chain or branched alkyl, alkoxy or acyl having in each case up to 5 carbon atoms, or denotes a radical of the formula $$W\diagup\hspace{-0.3em}\diagdown N-(CH_2)e-$$

wherein e has the abovementioned meaning of d and is identical to or different from this, W has the abovementioned meaning of T and is identical to or different from this, or $R^{22}$ denotes phenyl or pyridyl, c denotes a number 0, 1 or 2, $R^{23}$ denotes straight-chain or branched alkyl or alkenyl having up to 16 carbon atoms, which is optionally substituted by straight-chain or branched alkoxycarbonyl having up to 6 carbon atoms or phenyl or by a 5- to 7-membered aromatic heterocyclic radical having up to 3 hetero atoms from the series consisting of S, N and O, or denotes aryl having 6 to 10 carbon atoms or a 5- to 7-membered aromatic heterocyclic radical having up to 3 hetero atoms from the series consisting of S, N and O, and wherein the abovementioned cyclic radicals are optionally substituted up to twice in an identical or different manner by carboxyl, halogen, cyano, formyl, trifluoromethyl, nitro, straight-chain or branched alkoxy, alkoxycarbonyl, alkylthio or acyl having in each case up to 6 carbon atoms or by straight-chain or branched alkyl having up to 6 carbon atoms, or $R^2$ represents morpholinyl, or represents a radical of the formula wherein $R^{31}$ and $R^{32}$ have the abovementioned meaning of $R^{24}$ and $R^{25}$ and are identical to or different from these, $R^{33}$ and $R^{34}$ together form a radical of the formula =O or $R^{33}$ and $R^{34}$ are identical or different and denote hydrogen, hydroxyl or straight-chain or branched alkyl having up to 6 carbon atoms, which is optionally substituted by a group of the formula —$NR^{41}R^{42}$ wherein $R^{41}$ and $R^{42}$ have the abovementioned meaning of $R^{24}$ and $R^{25}$ and are identical to or different from these, f denotes the number 0 or 1, g denotes the number 0, 1, 2, 3, 4, 5 or 6, $R^{35}$ denotes aryl having 6 to 10 carbon atoms or a 5- to 6-membered aromatic, optionally also benzo-fused heterocyclic radical having up to 3 hetero atoms from the series consisting of S, N and/or O, it being possible for all the ting systems to be substituted up to 3 times in an identical or different manner by nitro, cyano, hydroxyl, phenyl, halogen, trifluoromethyl or by straight-chain or branched alkyl, alkoxy or acyl having in each case up to 5 carbon atoms, or $R^{35}$ denotes morpholinyl, hydroxyl, straight-chain or branched alkoxy having up to 6 carbon atoms or a radical of the formula

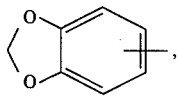

$NR^{43}R^{44}$ or —CO—$R^{45}$, wherein $R^{43}$ and $R^{44}$ are identical or different and have the abovementioned meaning of $R^{24}$ and $R^{25}$, $R^{45}$ denotes morpholinyl, hydroxyl or straight-chain or branched alkoxy having up to 6 carbon atoms, $R^{36}$ and $R^{37}$ are identical or different and denote hydrogen, phenyl or straight-chain or branched alkyl having up to 6 carbon atoms or benzyl, $R^{36}$, $R^{39}$ and $R^{40}$ are identical or different and have the abovementioned meaning of $R^{30}$ and are identical to or different from this, l denotes the number 1 or 2, and salts thereof.

Physiologically acceptable salts of the benzoxazolyl and benzothiazolyloxazolidinones can be salts of the substances according to the invention with mineral acids, carboxylic acids or sulphonic acids. Salts which are particularly preferred are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts which can be mentioned are salts with customary bases, such as, for example, alkali metal salts (for example sodium or potassium salts), alkaline earth metal salts (for example calcium or magnesium salts) or ammonium salts derived from ammonia or organic amines, such as, for example, diethylamine, triethylamine, ethyldiisopropylamine, procaine, dibenzylamine, N-methylmorpholine, dihydroabiethylamine, 1-ephenamine or methyl-piperidine, or pyridinium salts.

Reactions products with $C_1$–$C_4$-alkyl halides, in particular $C_1$–$C_4$-alkyl iodides, can furthermore function as salts.

A heterocyclic radical is in general a 5- to 6-membered, saturated or unsaturated ring which can contain, as hetero atoms, up to 3 oxygen, sulphur and/or nitrogen atoms. Preferred radicals which are mentioned are: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl or piperazinyl.

These also include 5- to 6-membered saturated heterocyclic radicals which are bonded via N and can furthermore contain, as hetero atoms, up to 2 oxygen, sulphur and/or nitrogen atoms, such as, for example, piperidyl, morpholinyl or piperazine or pyrrolidinyl. Piperidyl and pyrrolidinyl are particularly preferred.

A hydroxy-protective group in the context of the abovementioned definition is in general a protective group from the series consisting of: trimethylsilyl, triisopropylsilyl, tert-butyl-dimethylsilyl, benzyl, benzyloxycarbonyl, 2-nitrobenzyl, 4-nitrobenzyl, tert-butyloxycarbonyl, allyloxycarbonyl, 4-methoxybenzyl, 4-methoxybenzyloxycarbonyl, tetrahydropyranyl, formyl, acetyl, trichloroacetyl, 2,2,2-trichloroethoxycarbonyl, methoxyethoxymethyl, [2-(trimethylsilyl)ethoxy]methyl, benzoyl, 4-methylbenzoyl, 4-nitrobenzoyl, 4-fluorobenzoyl, 4-chlorobenzoyl and 4-methoxybenzoyl. Acetyl, tert-butyldimethylsilyl and tetrahydropyranyl are preferred.

Amino-protective groups in the context of the invention are the customary amino-protective groups used in peptide chemistry.

These include, preferably: benzyloxycarbonyl, 2,4-dimethoxybenzyloxycarbonyl, 4-methoxybenzyloxycarbonyl, methoxycarbonyl, ethoxycarbonyl, tert-butoxy-carbonyl, allyloxycarbonyl, phthaloyl, 2,2,2-trichloroethoxycarbonyl, fluorenyl-9-methoxycarbonyl, formyl, acetyl, 2-chloroacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl and benzyloxymethylene, 4-nitrobenzyl, 2,4-dinitrobenzyl, 4-nitrophenyl, 4-methoxyphenyl and triphenylmethyl.

The compounds according to the invention can exist in stereoisomeric forms which either behave as minor images (enantiomers) or do not behave as mirror images (diastereomers). The invention relates both to the enantiomers or diastereomers and to particular mixtures thereof. The racemic forms, like the diastereomers can be separated into the stereoisomerically uniform constituents in the known manner.

Preferred compounds of the general formula (I) are those in which

A represents an oxygen atom, or represents a radical of the formula —$S(O)_a$, wherein a denotes the number 0 or 2, $R^1$ represents azido, or represents a group of the formula —$OSO_2R^3$ or —$NR^4R^5$, wherein $R^3$ denotes straight-chain or branched alkyl having up to 3 carbon atoms, phenyl or tolyl, $R^4$ and $R^5$ are identical or different and denote cyclopropyl, cyclopentyl, cyclohexyl, hydrogen, phenyl or straight-chain or branched alkyl or alkoxy having in each case up to 6 carbon atoms, tert-butoxycarbonyl or benzyloxycarbonyl, or $R^4$ or $R^5$ denotes a group of the formula —CO—$R^6$, wherein $R^6$ denotes cyclopropyl, cyclobutyl, cyclopentyl, cyclohexyl or straight-chain or branched alkyl or alkoxy having in each case up to 6 carbon atoms, phenyl or hydrogen, G, L and M are identical or different and represent hydrogen, carboxyl, fluorine, chlorine, bromine, iodine, cyano, trifluoromethyl, formyl, nitro or straight-chain or branched alkoxy, alkoxycarbonyl, alkylthio or acyl having in each case up to 3 carbon atoms, or represent straight-chain or branched alkyl having up to 4 carbon atoms, which can in turn be substituted by hydroxyl, by straight-chain or branched alkoxy or acyl having up to 4 carbon atoms or by a group of the formula —$NR^7R^8$, wherein $R^7$ and $R^8$ are identical or different and denote hydrogen, straight-chain or branched alkyl having up to 3 carbon atoms or phenyl, or together with the nitrogen atom form a morpholinyl, pyrrolidinyl, piperazinyl or piperidyl ring, each of which is optionally substituted, including via the free N function, by methyl, ethyl or acetyl, and/or optionally represent a group of the formula —NR$^{7'}$R$^{8'}$, wherein R$^{7'}$ and R$^{8'}$ have the abovementioned meaning of R$^7$ and R$^8$ and are identical to or different from these, and/or optionally represent (C$_2$–C$_4$)-alkenylphenyl, phenyl, pyridyl or thienyl, each of which is in turn optionally substituted by a group of the formula —CO—NR$^9$R$^{10}$, —NR$^{11}$R$^{12}$, —NR$^{13}$—SO$_2$—R$^{14}$, R$^{15}$R$^{16}$N—SO$_2$— or R$^{17}$—S(O)$_b$—wherein b denotes the number 0, 1 or 2, R$^9$, R$^{10}$, R$^{13}$, R$^{15}$ and R$^{16}$ are identical or different and denote hydrogen, straight-chain or branched alkyl having up to 4 carbon atoms or phenyl, R$^{11}$ and R$^{12}$ are identical or different and have the abovementioned meaning of R$^7$ and R$^8$ and are identical to or different from these, R$^{14}$ and R$^{17}$ are identical or different and have the abovementioned meaning of R$^3$ and are identical to or different from this, and/or are in turn optionally substituted up to twice in an identical or different manner by carboxyl, fluorine, chlorine, bromine, iodine, cyano, trifluoromethyl, formyl, nitro, phenyl, or straight-chain or branched alkoxy, alkoxycarbonyl, alkylthio or acyl having in each case up to 4 carbon atoms, or by straight-chain or branched alkyl having up to 4 carbon atoms, which can in turn optionally be substituted by hydroxyl, by straight-chain or branched alkoxy or acyl having up to 4 carbon atoms or by a group of the formula —NR$^{18}$R$^{19}$, wherein R$^{18}$ and R$^{19}$ have the abovementioned meaning of R$^7$ and R$^8$ and are identical to or different from these, R$^2$ represents hydrogen, formyl or carboxyl, or represents straight-chain or branched alkoxycarbonyl having up to 5 carbon atoms, or represents straight-chain or branched alkyl or alkenyl having in each case up to 6 carbon atoms, each of which is optionally substituted by hydroxyl, fluorine, chlorine, bromine or by straight-chain or branched alkoxy, acyl, alkylthio or alkoxycarbonyl having in each case up to 6 carbon atoms, or by phenyl, which can in turn by substituted by fluorine, chlorine or bromine, or represents phenyl, which is optionally substituted by carboxyl, fluorine, chlorine, bromine, iodine, cyano, trifluoromethyl, formyl, nitro or straight-chain or branched alkoxy, alkoxycarbonyl, alkylthio or acyl having in each case up to 4 carbon atoms, or by straight-chain or branched alkyl having up to 4 carbon atoms, or represents a radical of the formula —NR$^{20}$R$^{21}$, —OR$^{22}$ or —S(O)$_c$—R$^{23}$, wherein R$^{20}$ denotes cyclopropyl, cyclopentyl, cyclohexyl, phenyl, straight-chain or branched acyl having up to 4 carbon atoms or straight-chain or branched alkyl having up to 6 carbon atoms, which is optionally substituted by hydroxyl, straight-chain or branched alkoxy or hydroxy-substituted alkoxy having in each case up to 5 carbon atoms, pyridyl, pyrazinyl, pyrimidyl or by phenyl, which can in turn be substituted by hydroxyl, trifluoromethyl, fluorine, chlorine, bromine, nitro or by straight-chain or branched alkoxy having up to 3 carbon atoms, or alkyl is optionally substituted by a radical of the formula —NR$^{24}$R$^{25}$ or

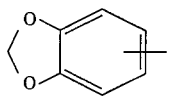

wherein

R$^{24}$ and R$^{58}$ are identical or different and denote hydrogen or straight-chain or branched alkyl having up to 3 carbon atoms, or R$^{20}$ denotes a radical of the formula

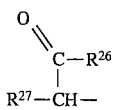

wherein

R$^{26}$ denotes hydroxyl, straight-chain or branched alkoxy having up to 3 carbon atoms or a radical of the formula —NR$^{28}$R$^{29}$, wherein R$^{28}$ and R$^{29}$ are identical or different and denote hydrogen or straight-chain or branched alkyl having up to 3 carbon atoms, cyclopropyl, cyclopentyl, cyclohexyl or phenyl, R$^{27}$ denotes hydrogen or straight-chain or branched alkyl having up to 5 carbon atoms, which is optionally substituted by phenyl, or R$^{20}$ denotes a radical of the formula

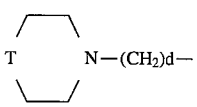

wherein d denotes the number 0, 1, 2 or 3,

T denotes an oxygen atom or a group of the formula —CH$_2$ or —NR$^{30}$, wherein R$^{30}$ denotes hydrogen, phenyl or straight-chain or branched alkyl having up to 4 carbon atoms, which is optionally substituted by hydroxyl, and R$^{21}$ has the abovementioned meaning of R$^{20}$ and is identical to or different from this, or denotes hydrogen, R$^{22}$ denotes straight-chain or branched alkyl having up to 6 carbon atoms, which is optionally substituted by straight-chain or branched alkoxy or hydroxy- or alkoxy-substituted alkoxy having in each case up to 5 carbon atoms, cyclopropyl, cyclopentyl, cyclohexyl, pyridyl, pyrimidyl, pyrazinyl or quinolyl, each of which can in turn be substituted by nitro, trifluoromethyl, fluorine, chlorine, bromine, cyano, hydroxyl or by straight-chain or branched alkyl, alkoxy or acyl having in each case up to 4 carbon atoms, or R$^{22}$ denotes a radical of the formula

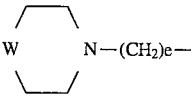

wherein e has the abovementioned meaning of d and is identical to or different from this, W has the abovementioned meaning of T and is identical to or different from this, or $R^{22}$ denotes phenyl or pyridyl, c denotes the number 0, 1 or 2, $R^{23}$ denotes straight-chain or branched alkyl or alkenyl having in each case up to 14 carbon atoms, which is optionally substituted by straight-chain or branched alkoxycarbonyl having up to 4 carbon atoms or by phenyl, thienyl, furyl, pyrrolyl, imidazolyl, pyridyl, pyrazinyl, pyrimidyl or pyridazinyl, or denotes phenyl, thienyl, furyl, pyrrolyl, imidazolyl, pyridinyl, pyrazinyl, pyrimidyl or pyridazinyl, and wherein the abovementioned cyclic radicals are optionally substituted up to twice in an identical or different manner by carboxyl, fluorine, chlorine, bromine, iodine, cyano, trifluoromethyl, formyl, nitro, straight-chain or branched alkoxy, alkoxycarbonyl, alkylthio or acyl having in each case up to 4 carbon atoms or by straight-chain or branched alkyl having up to 4 carbon atoms, or $R^2$ represents morpholinyl, or represents a radical of the formula

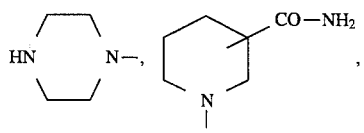

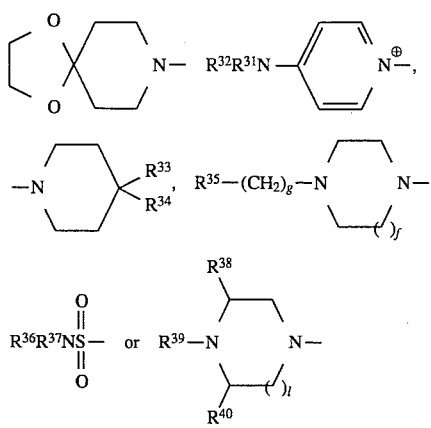

wherein $R^{31}$ and $R^{32}$ have the abovementioned meaning of $R^{24}$ and $R^{25}$ and are identical to or different from these, $R^{33}$ and $R^{34}$ together form a radical of the formula =O or $R^{33}$ and $R^{34}$ are identical or different and denote hydrogen, hydroxyl or straight-chain or branched alkyl having up to 4 carbon atoms, which is optionally substituted by a group of the formula —$NR^{41}R^{42}$, wherein $R^{41}$ and $R^{42}$ have the abovementioned meaning of $R^{24}$ and $R^{25}$ and are identical to or different from these, f denotes the number 0 or 1, g denotes the number 0, 1, 2, 3 or 4, $R^{35}$ denotes phenyl, pyridyl, pyrimidyl, pyrazinyl or quinolyl, each of which can in turn be substituted up to twice in an identical or different manner by nitro, cyano, hydroxyl, phenyl, fluorine, chlorine, bromine, trifluoromethyl or by straight-chain or branched alkyl, alkoxy or acyl having in each case up to 4 carbon atoms, or $R^{35}$ denotes morpholinyl, hydroxyl, straight-chain or branched alkoxy having up to 4 carbon atoms or a radical of the formula

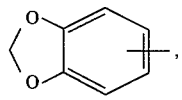

$NR^{43}R^{44}$ or —CO— $R^{45}$, wherein $R^{43}$ and $R^{44}$ are identical or different and have the abovementioned meaning of $R^{24}$ and $R^{25}$, $R^{45}$ denotes morpholinyl, hydroxyl or straight-chain or branched alkoxy having up to 5 carbon atoms, $R^{36}$ and $R^{37}$ are identical or different and denote hydrogen, phenyl or straight-chain or branched alkyl having up to 4 carbon atoms or benzyl, $R^{38}$, $R^{39}$ and R' are identical or different and have the abovementioned meaning of $R^{30}$ and are identical to or different from this, l denotes the number 1 or 2, and salts thereof.

Particularly preferred compounds of the general formula (I) are those in which

A represents an oxygen atom, or represents a radical of the formula —$S(O)_a$, wherein a denotes the number 0 or 2, $R^1$ represents azido, or represents a group of the formula —$OSO_2R^3$ or —$NR^4R^5$, wherein $R^3$ denotes methyl, ethyl, phenyl or tolyl, $R^4$ and $R^5$ are identical or different and denote cyclopropyl, cyclopentyl, cyclohexyl, hydrogen, phenyl or straight-chain or branched alkyl having up to 5 carbon atoms, or wherein $R^4$ or $R^5$ denote a group of the formula —CO—$R^6$, wherein $R^6$ denotes cyclopropyl, cyclopentyl, cyclohexyl or straight-chain or branched alkyl or alkoxy having in each case up to 4 carbon atoms, hydrogen or phenyl, G, L and M are identical or different and represent hydrogen, carboxyl, fluorine, chlorine, bromine, iodine, cyano, formyl or nitro, or represent straight-chain or branched alkyl having up to 3 carbon atoms, and/or represent a group of the formula —$NR^{7'}R^{8'}$, wherein $R^{7'}$ and $R^{8'}$ are identical or different and denote hydrogen or methyl, represents hydrogen, formyl, carboxyl or straight-chain or branched alkoxycarbonyl having up to 3 carbon atoms, or represents straight-chain or branched alkyl or alkenyl having in each case up to 4 carbon atoms, each of which is optionally substituted by hydroxyl, fluorine, chlorine, bromine or by straight-chain or branched alkoxy, acyl, alkylthio or alkoxycarbonyl having in each case up to 3 carbon atoms or by phenyl, which can in turn be substituted by chlorine, or represents phenyl, which is optionally substituted by carboxyl, fluorine, chlorine, bromine, iodine, cyano, formyl, trifluoromethyl, nitro, straight-chain or branched alkoxy, alkoxycarbonyl or acyl having in each case up to 3 carbon atoms or by straight-chain or branched alkyl having up to 3 carbon atoms, or represents a radical of the formula —$NR^{20}R^{21}$, —$OR^{22}$ or —$S(O)_c$—$R^{23}$, wherein $R^{20}$ denotes cyclopropyl, cyclopentyl, cyclohexyl, phenyl, straight-chain or branched acyl having up to 3 carbon atoms, or straight-chain or branched alkyl having up to 4 carbon atoms, which is optionally substituted by hydroxyl, straight-chain or branched alkoxy or hydroxy-substituted alkoxy having in each case up to 3 carbon atoms, pyridyl, pyrimidyl or pyrazinyl, or by phenyl, which can in turn be substituted by hydroxyl, trifluoromethyl, fluorine, chlorine, bromine, nitro, methoxy or ethoxy, or alkyl is optionally substituted by a radical of the formula $-NR^{24}R^{25}$ or

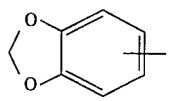

wherein $R^{24}$ and $R^{25}$ are identical or different and denote hydrogen, methyl or ethyl, or $R^{20}$ denotes a radical of the formula

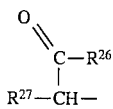

wherein $R^{26}$ denotes hydroxyl, methoxy, ethoxy or a radical of the formula $-NR^{28}R^{29}$, wherein $R^{28}$ and $R^{29}$ are identical or different and denote hydrogen, methyl, ethyl, cyclopropyl or phenyl, $R^{27}$ denotes hydrogen or straight-chain or branched alkyl having up to 3 carbon atoms, which is optionally substituted by phenyl, or $R^{20}$ denotes a radical of the formula

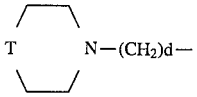

wherein d denotes the number 0, 1, 2 or 3,

T denotes an oxygen atom or a group of the formula $-CH_2$ or $-NR^{30}$, wherein $R^{30}$ denotes hydrogen or straight-chain or branched alkyl having up to 3 carbon atoms, which is optionally substituted by hydroxyl, and $R^{21}$ has the abovementioned meaning of $R^{20}$ and is identical to or different from this, or denotes hydrogen, $R^{22}$ denotes straight-chain or branched alkyl having up to 4 carbon atoms, which is optionally substituted by straight-chain or branched alkoxy or hydroxy- or alkoxy-substituted alkoxy having in each case up to 4 carbon atoms, cyclopropyl, cyclopentyl, cyclohexyl, pyridyl, pyrazinyl or pyrimidyl, which can in turn be substituted by nitro, trifluoromethyl, fluorine, chlorine, bromine, cyano, hydroxyl or by straight-chain or branched alkyl, alkoxy or acyl having in each case up to 3 carbon atoms, or $R^{22}$ denotes a radical of the formula

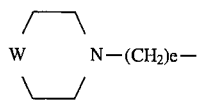

wherein e has the abovementioned meaning of d and is identical to or different from this, W has the abovementioned meaning of T and is identical to or different from this, or $R^{22}$ denotes phenyl or pyridyl, c denotes the number 0, 1 or 2, $R^{23}$ denotes straight-chain or branched alkyl or alkenyl having up to 13 carbon atoms, which is optionally substituted by straight-chain or branched alkoxycarbonyl having up to 3 carbon atoms or phenyl or by thienyl, pyridyl, pyrazinyl or pyrimidyl, or denotes phenyl, thienyl, pyridyl, pyrazinyl or pyrimidyl, and in which the abovementioned cyclic radicals are optionally substituted by carboxyl, fluorine, chlorine, bromine, iodine, cyano, formyl, trifluoromethyl, nitro, straight-chain or branched alkoxy, alkoxycarbonyl or acyl having in each case up to 4 carbon atoms or by straight chain or branched alkyl having up to 4 carbon atoms, or $R^2$ represents morpholinyl, or represents a radical of the formula

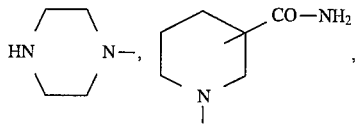

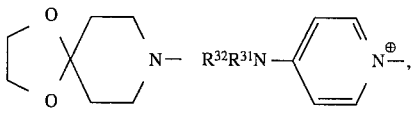

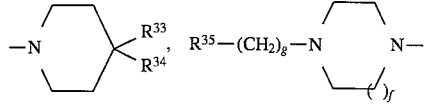

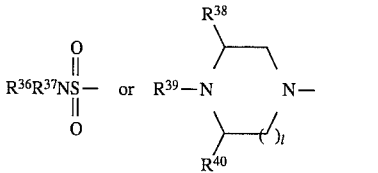

wherein $R^{31}$ and $R^{32}$ have the abovementioned meaning of $R^{24}$ and $R^{25}$ and are identical to or different from these, $R^{33}$ and $R^{34}$ together form a radical of the formula $=O$ or $R^{33}$ and $R^{34}$ are identical or different and denote hydrogen, hydroxyl or straight-chain or branched alkyl having up to 3 carbon atoms, which is optionally substituted by a group of the formula $-NR^{41}R^{42}$, wherein $R^{41}$ and $R^{42}$ have the abovementioned meaning of $R^{24}$ and $R^{25}$ and are identical to or different from these, f denotes the number 0 or 1, g denotes the number 0, 1, 2 or 3, $R^{35}$ denotes phenyl, pyridyl, pyrazinyl or pyrimidyl, each of which can in turn be substituted by nitro, cyano, hydroxyl, phenyl, fluorine, chlorine, bromine, trifluoromethyl or by straight-chain or branched alkyl, alkoxy or acyl having in each case up to 3 carbon atoms, or $R^{35}$ denotes morpholinyl, hydroxyl, straight-chain or branched alkoxy having up to 3 carbon atoms or a radical of the formula

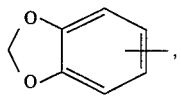

—$NR^{43}R^{44}$ or —$CO$—$R^{45}$, wherein $R^{43}$ and $R^{44}$ are identical or different and have the abovementioned meaning of $R^{24}$ and $R^{25}$, $R^{45}$ denotes morpholinyl, hydroxyl or straight-chain or branched alkoxy having up to 4 carbon atoms, $R^{36}$ and $R^{37}$ are identical or different and denote hydrogen, phenyl or straight-chain or branched alkyl having up to 3 carbon atoms or benzyl, $R^{38}$, $R^{39}$ and $R'$ are identical or different and have the abovementioned meaning of $R^{30}$ and are identical to or different from this, I denotes the number 1 or 2, and salts thereof.

Especially preferred compounds of the general formula (I) are those in which

G, L and M represent hydrogen and the oxazolidinone radical is bonded to the phenyl ring in positions 5 or 6.

Processes for the preparation of the compounds of the general formula (I) according to the invention have furthermore been found, characterized in that

[A] compounds of the general formula (II)

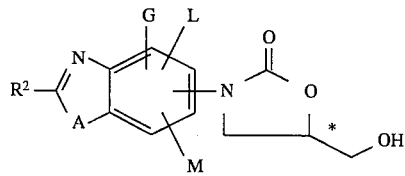

in which

A, G, L, M and $R^2$ have the abovementioned meaning, are first converted, by reaction with $(C_1$–$C_4)$-alkyl- or phenylsulphonic acid chlorides in inert solvents and in the presence of a base, into the corresponding compounds of the general formula (Ia)

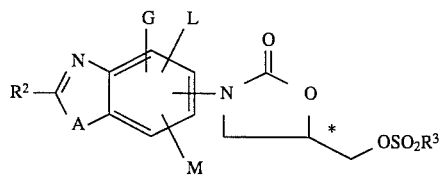

in which

A, G, L, M, $R^2$ and $R^3$ have the abovementioned meaning, the azides of the general formula (Ib)

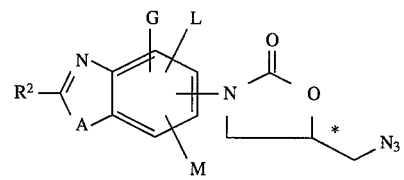

in which

A, G, L, M and $R^2$ have the abovementioned meaning, are then prepared with sodium azide in inert solvents, and in a further step, by reaction with $(C_1$–$C_4$—$O)_3$—P or $Ph_3P$, preferably $(CH_3O)_3P$, in inert solvents and with acids, are converted into the amines of the general formula (Ic)

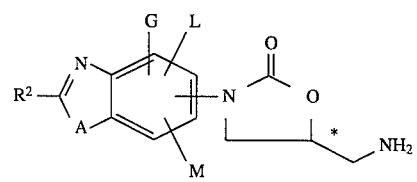

in which

A, G, L, M and $R^2$ have the abovementioned meaning, and, by reaction with acetic anhydride, acetyl chloride or other acylating agents of the general formula (III)

Y—CO—$R^6$ (III)

in which $R^6$ has the abovementioned meaning and

Y represents halogen, preferably chlorine, or represents the radical —$OCOR^6$, in inert solvents, the compounds of the general formula (Id)

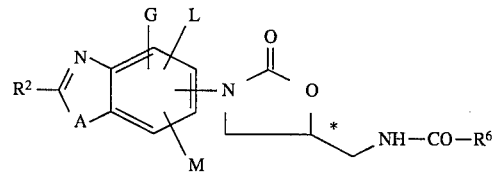

in which

A, G, L, M, $R^2$ and $R^6$ have the abovementioned meaning, are prepared and in the case of the S-oxides, starting from the corresponding S-alkyl compounds, are oxidized with m-chloroperbenzoic acid [B], and in the case of substitution reactions, starting from the sulphonyl compounds, nucleophiles are introduced with substitution [C], and, if appropriate, an alkyl-halogenation is carried out by customary methods [D], and, if appropriate, starting from the compounds where $R^2$=2-phenylvinyl, oxidation is first carried out to give the corresponding formyl derivatives, and in a second step reduction is carried out by known methods [E], and in the case where $R^4$, $R^5$, $R^7$, $R^{7'}$, $R^8$, $R^{8'}$, $R^9$, $R^{10}$, $R^{11}$, $R^{12}$, $R^{13}$, $R^{15}$, $R^{16}$, $R^{18}$, $R^{19}$, $R^{21}$, $R^{24}$, $R^{25}$, $R^{31}$, $R^{32}$, $R^{41}$, $R^{42}$, $R^{43}$ and/or $R_{44}$≠H, if appropriate an alkylatio is carried out by customary methods, and, if appropriate, other substituents or functional groups which are already present are introduced or, respectively, derivatized by customary methods, such as, for example, redox reactions, substitution reactions and/or hydrolysis reactions or introduction and breakdown of protective groups.
Processes according to the invention can be illustrated by way of example by the following equations:
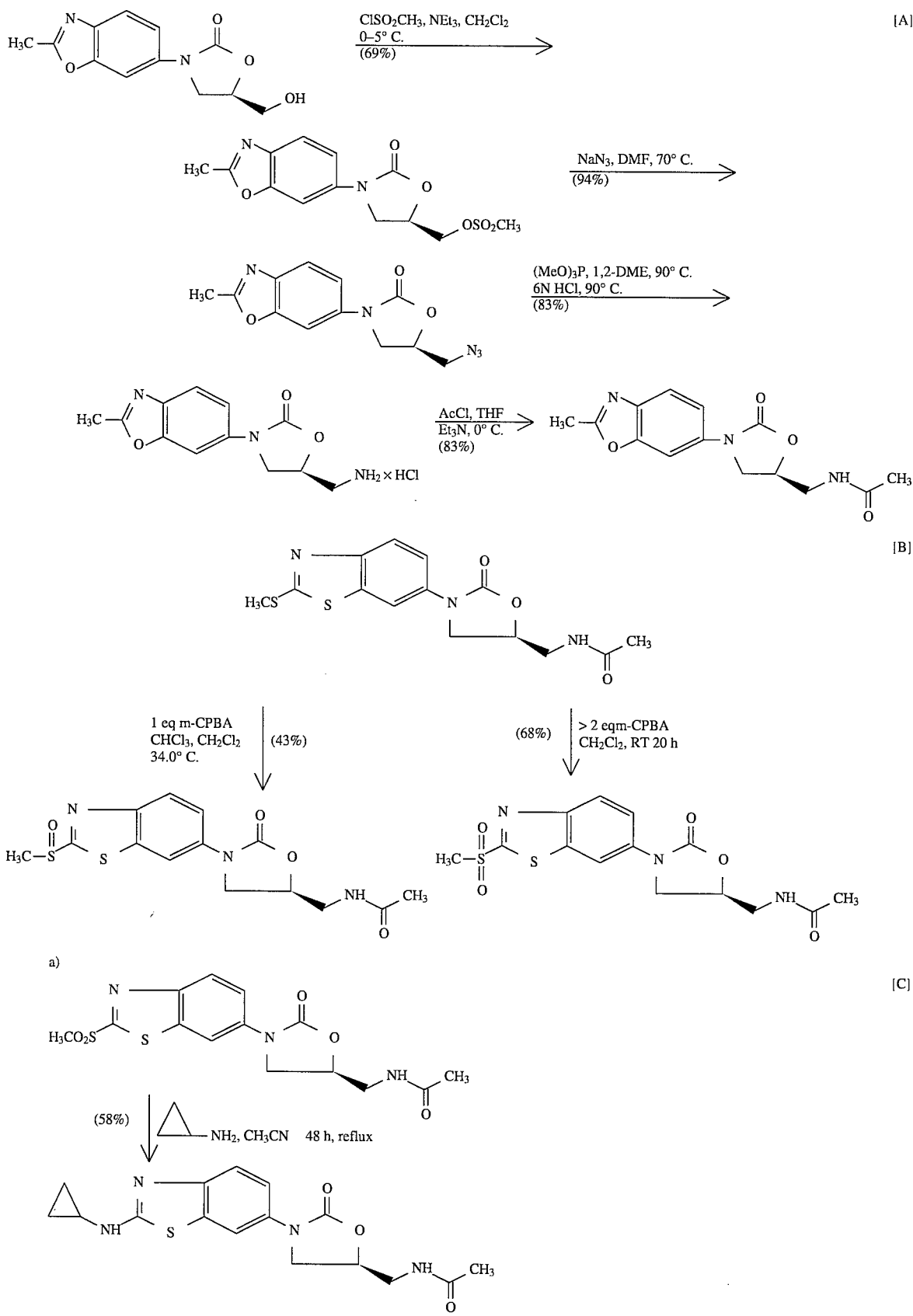

b)
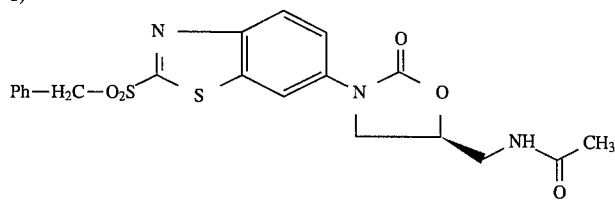
(44%) ↓ 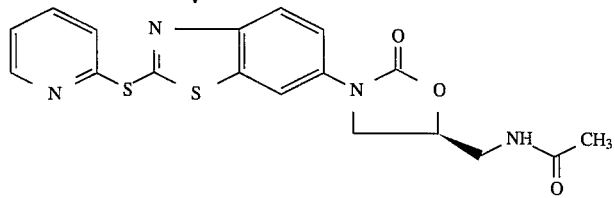 SH, NEt₃, CH₃CN, 21 h 60° C.
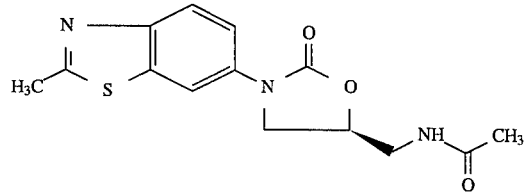
↓ SO₂Cl₂, cat AIBN, 11 h, 90° C.
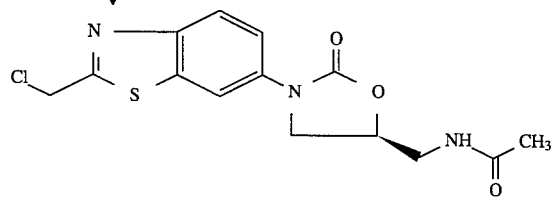
[D]
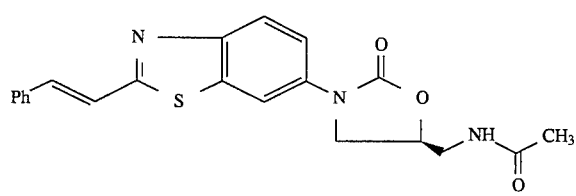
[E]
↓ 1.) O₃, CH₂Cl₂ −78° C.
2.) (CH₃)₂S, RT
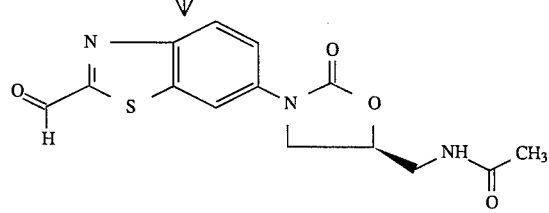
↓ NaBH₄
MeOH, 0° C.

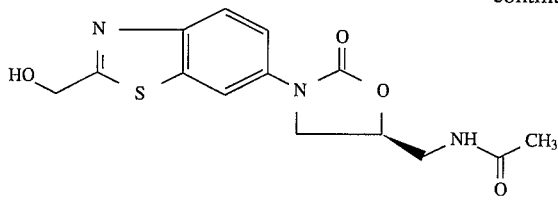

Suitable solvents are, depending on the individual process steps, the customary solvents which do not change under the reaction conditions. These include, preferably, alcohols, such as methanol, ethanol, propanol or isopropanol, or ethers, such as diethyl ether, dioxane, 1,2-dimethoxyethane, tetrahydrofuran, glycol dimethyl ether or tert-butyl methyl ether, or ketones, such as acetone or butanone, or amides, such as dimethylformamide or hexamethyl-phosphoric acid triamide, or hydrocarbons, such as hexane, benzene, dichlorobenzene, xylene or toluene, or dimethyl sulphoxide, acetonitrile, ethyl acetate or halogenated hydrocarbons, such as methylene chloride, chloroform or carbon tetrachloride, or pyridine, picoline or N-methylpiperidine. Mixtures of the solvents mentioned can also be used.

Suitable bases are, depending on the individual process steps, the customary inorganic or organic bases. These include, preferably, alkali metal hydroxides, such as, for example, sodium hydroxide or potassium hydroxide, or alkali metal carbonates, such as sodium carbonate or potassium carbonate, or alkali metal alcoholates, such as, for example, sodium methanolate or potassium methanolate or sodium ethanolate or potassium ethanolate, or organic amines, such as ethyldiisopropylamine, triethylamine, picoline, pyridines or N-methylpiperidine, or amides, such as sodium amide or lithium diisopropylamide, or lithium N-silylalkylamides, such as, for example, lithium N-(bis-)triphenylsilylamide, or lithium alkyls, such as n-butyllithium.

The base is employed in an amount of 1 mol to 10 mol, preferably 1 mol to 3 mol, per mole of the compounds of the general formula (II).

All the reactions are in general carried out under normal, increased or reduced pressure (for example 0.5 to 5 bar). They are in general carded out under normal pressure.

The oxidation [B] is in general carried out in one of the abovementioned solvents, preferably in methylene chloride, with oxidizing agents such as, for example, metachloroperbenzoic acid, hydrogen peroxide or peracetic acid, preferably with metachloroperbenzoic acid, in a temperature range from 0° C. to 80° C., preferably from 0° C. to 40° C.

The substitution [C] is in general carded out in one of the abovementioned solvents, preferably acetonitrile, and in the presence of one of the abovementioned C1–C4-alkylamine bases, preferably triethylamine, in a temperature range from +20° C. to 80° C., preferably at 60° C. to 80° C., and under normal pressure. In the case where R2=OR22, the reaction of the sulphone with the corresponding alcoholate is in general carried out in the presence of hydrides, preferably potassium hydride, in one of the abovementioned solvents, preferably dimethylformamide.

The alkyl-halogenation [D] is in general carded out with halogenating agents, such as, for example, N-bromo-succinimide or sulfuryl chloride, preferably sulfuryl chloride, in the presence of a catalyst, such as, for example, dibenzoyl peroxide or azobisisobutyronitrile, preferably azobisisobutyronitrile, in a temperature range from +60° C. to +130° C., preferably at +70° C. to +90° C, and under normal pressure.

The oxidation to the formyl derivatives [E] is in general carried out with $O_3$ and then $(CH_3)_2S$ in one of the abovementioned halogenated hydrocarbons, preferably methylene chloride and methanol, in a temperature range from −78° C. to +40° C. and under normal pressure.

The reductions are in general carried out with hydrides in inert solvents or with boranes, diboranes or their complex compounds.

The reductions are preferably carried out with hydrides, such as complex boron hydrides or aluminium hydrides, and boranes. Sodium borohydride, lithium borohydride, sodium cyanoborohydride, lithium aluminium hydride, sodium bis-(2-methoxyethoxy)aluminium hydride or boron-tetrahydrofuran are particularly preferably employed here.

The reduction is in general carried out in a temperature range from −50° C. to the particular boiling point of the solvent, preferably from −20° C. to +90° C.

The reductions can in general be carded out by means of hydrogen in water or in inert organic solvents, such as alcohols, ethers or halogenated hydrocarbons, or mixtures thereof, using catalysts such as Raney nickel, palladium, palladium-on-animal charcoal or platinum, or with hydrides or boranes in inert solvents, if appropriate in the presence of a catalyst.

The reaction is preferably carried out with hydrides, such as complex boron hydrides or aluminium hydrides. Sodium borohydride, lithium aluminium hydride or sodium cyano borohydride are particularly preferably employed here.

Suitable solvents here are all the inert organic solvents which do not change under the reaction conditions. These include, preferably, alcohols, such as methanol, ethanol, propanol or isopropanol, or ethers, such as diethyl ether, dioxane, tetrahydrofuran, glycol dimethyl ether or diethylene glycol dimethyl ether, or amides, such as hexamethylphosphoric acid triamide or dimethylformamide, or acetic acid. It is also possible to use mixtures of the solvents mentioned. Methanol is particularly preferred.

The hydroxy-protective groups are in general split up by customary methods, for example by hydrogenolytic cleavage of the benzyl ethers with hydrogen gas in the abovementioned inert solvents in the presence of a catalyst.

The amino-protective group is in general likewise split off by customary methods, and in particular Boc is preferably split off with hydrochloric acid in dioxane, Fmoc is split off with piperidine and Z is split off with HBr/HOAc or by hydrogenolysis.

The other abovementioned derivatization reactions are in general carried out by the methods published in Compendium of organic Synthetic Methods, T. T. Harrison and S. Harrison, Wiley Interscience.

Redox reactions, reductive amination, transesterification and halogenation of methyl groups with N-bromosuccinimide (NBS) or N-chlorosuccinimide (NCS), which are illustrated below by way of example, are mentioned as preferred.

Suitable solvents for the alkylation are the customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, or triethylamine, pyridine, dimethyl sulphoxide, dimethylformamide, acetonitrile, acetone or nitromethane. It is also possible to use mixtures of the solvents mentioned. Methylene chloride, dimethyl sulphoxide and dimethylformamide are preferred.

The alkylation is carried out in the abovementioned solvents at temperatures from 0° C. to +150° C., preferably at room temperatures up to +100° C., and under normal pressure.

The amidation and the sulphoamidation are in general carried out in inert solvents in the presence of a base and a dehydrating agent.

Suitable solvents here are inert organic solvents which do not change under the reaction conditions. These include halogenated hydrocarbons, such as methylene chloride, chloroform, carbon tetrachloride, 1,2-dichloroethane, trichloroethane, tetrachloroethane, 1,2-dichloroethane or trichloroethylene, hydrocarbons, such as benzene, xylene, toluene, hexane, cyclohexane or petroleum fractions, nitromethane, dimethylformamide, acetonitrile or tetrahydrofuran. It is also possible to employ mixtures of the solvents. Methylene chloride and tetrahydrofuran are particularly preferred.

Suitable bases for the amidation and the sulphoamidation are the customary basic compounds. These include, preferably, alkali metal and alkaline earth metal hydroxides, such as lithium hydroxide, sodium hydroxide, potassium hydroxide or barium hydroxide, alkali metal hydroxides, such as sodium hydride, alkali metal or alkaline earth metal carbonates, such as sodium carbonate or potassium carbonate, or alkali metal alcoholates, such as, for example, sodium methanolate or ethanolate, potassium methanolate or ethanolate or potassium tert-butylate, or organic amines, such as benzyl trimethylammonium hydroxide, tetrabutylammonium hydroxide, pyridine, triethylamine or N-methylpiperidine.

The amidation and the sulphoamidation are in general carried out in a temperature range from 0° C. to 150° C., preferably at 25° C. to 40° C.

The amidation and the sulphoamidation are in general carried out under normal pressure. However, it is also possible to carry out the process under reduced pressure or under increased pressure (for example in a range from 0.5 to 5 bar).

In carrying out the amidation and the sulphoamidation, the base is in general employed in an amount of 1 to 3 mol, preferably 1 to 1.5 mol, per mole of the particular carboxylic acid.

Suitable dehydrating are carbodiimides, such as, for example, diisopropylcarbodiimide, dicyclohexylcarbodiimide or N-(3-dimethylaminopropyl)-N'-ethylcarbodiimide hydrochloride, or carbonyl compounds, such as carbonyldiimidazole, or 1,2-oxazolium compounds, such as 2-ethyl-5-phenyl-1,2-oxazolium 3-sulphonate, or propanephosphoric acid anhydride or isobutyl chloroformate or benzotriazolyloxy-tris-(dimethylamino)phosphonium hexafluorophosphate or phosphonic acid diphenyl ester amide or methanesulphonyl chloride, if appropriate in the presence of bases, such as triethylamine or N-ethylmorpholine or N-methylpiperidine or 4-dimethylaminopyridine.

Suitable bases for the hydrolysis are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate, or sodium bicarbonate. Sodium hydroxide or potassium hydroxide are particularly preferably employed.

Suitable solvents for the hydrolysis are water or the organic solvents customary for a hydrolysis. These include, preferably, alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is also possible to employ mixtures of the solvents mentioned.

The hydrolysis is in general carried out in a temperature range from 0° C. to +100° C., preferably from 20° C. to +80° C.

The hydrolysis is in general carried out under normal pressure. However, it is also possible to carry out the reaction under reduced pressure or under increased pressure (for example from 0.5 to 5 bar).

In carrying out the hydrolysis, the base is in general employed in an amount of 1 to 3 mol, preferably 1 to 1.5 mol, per mole of the ester. Molar amounts of the reactants are particularly preferably used.

The esterification is in general carried out with the corresponding alcohols in the presence of acids, preferably sulphuric acid, in a temperature range from 0° C. to 150° C., preferably from 50° C. to 100° C., and under normal pressure.

The compounds of the general formula (II) are partly included in the scope of meaning of PCT 93 081 79, but as concrete examples are for the most part new, and can be prepared, for example, by a process in which

[F] compounds of the general formulae (IV) or (V)

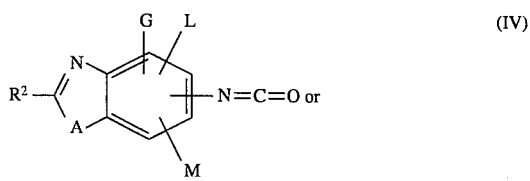

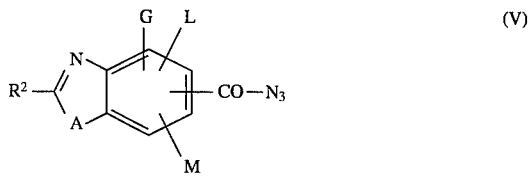

in which

A, G, L, M and $R^2$ have the abovementioned meaning, are reacted with lithium bromide$(C_4H_9)_3P(O)$ and epoxides of the general formula (VI)

in which

V represents $C_1$–$C_6$-acyloxy, in inert solvents, if appropriate in the presence of a base, and the hydroxyl function is liberated by a typical ester hydrolysis or by a typical transesterification, or

[G] compounds of the general formula (VII)

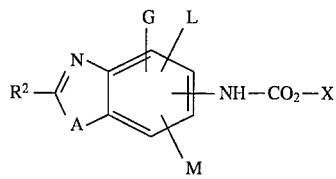

in which

A has the abovementioned meaning and

X represents a typical protective group, preferably benzyl, are reacted with epoxides of the general formula (VI) in inert solvents and in the presence of a base, for example lithium alkyls or lithium N-alkyl- or lithium N-silylalkylamides, preferably n-butyllithium, or

[H] compounds of the general formula (V) are first converted, by splitting off nitrogen in alcohols, into the compounds of the general formula (VIIa)

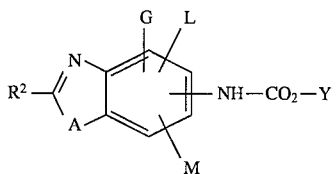

in which

A, G, L, M and $R^2$ have the abovementioned meaning and

Y represents straight-chain or branched $C_2$–$C_6$-alkyl, preferably n-butyl, and in a second step, as described under[G], the products are reacted with epoxides of the general formula (VI) in inert solvents in the presence of a base, preferably lithium N-alkyl- or N-silylalkylamides or n-butyllithium, or

[I] compounds of the general formula (VIII)

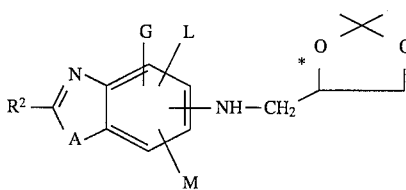

in which

A, G, L, M and $R^2$ have the abovementioned meaning, either are reacted directly with acids and diethyl carbonates, or the compounds of the general formula (IX)

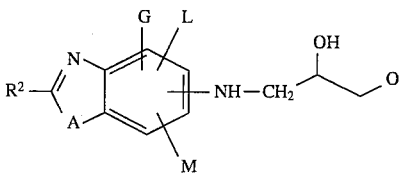

in which

A, G, L, M and $R^2$ have the abovementioned meaning, are first prepared by reaction of the compounds of the general formula (VIII) with acids, and are then cyclized in the presence of an auxiliary in inert solvents.

The processes according to the invention can be illustrated by way of example by the following equations:

[F]

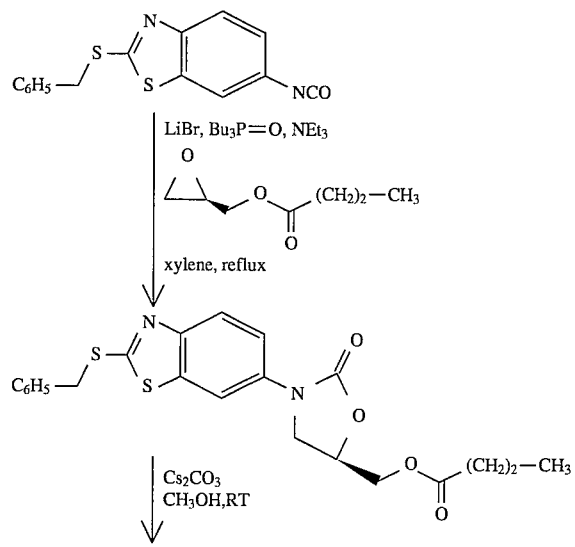

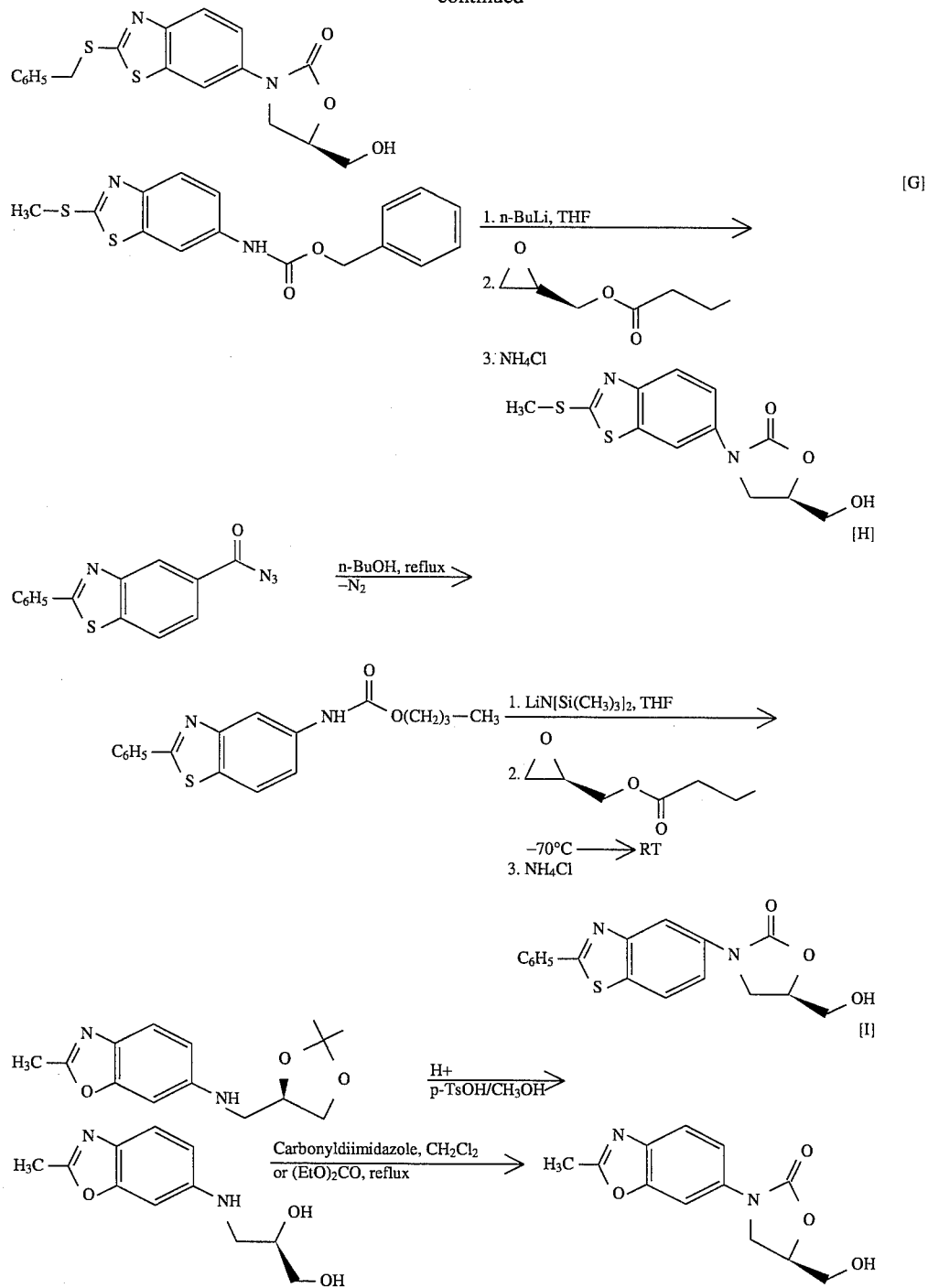

Suitable solvents are, depending on the individual process steps, the customary solvents which do not change under the reaction conditions. These include, preferably, alcohols, such as methanol, ethanol, propanol or isopropanol, or ethers, such as diethyl ether, dioxane, 1,2-dimethoxyethane, tetrahydrofuran, glycol dimethyl ether or tert-butylmethyl ether, or ketones, such as acetone or butanone, or amides, such as dimethylformamide or hexamethylphosphoric acid triamide, or hydrocarbons, such as hexane, benzene, dichlorobenzene, xylene or toluene, or dimethyl sulphoxide, acetonitrile, ethyl acetate or halogenated hydrocarbons, such as methylene chloride, chloroform or carbon tetrachloride, or pyridine, picoline or N-methylpiperidine. Mixtures of the solvents mentioned can also be used.

Suitable bases are, depending on the individual process steps, the customary inorganic or organic bases. These include, preferably, alkali metal hydroxides, such as, for example, sodium hydroxide or potassium hydroxide, or alkali metal carbonates, such as sodium carbonate or potassium carbonate, or alkali metal alcoholates, such as, for example, sodium methanolate or potassium methanolate or sodium ethanolate or potassium ethanolate, or organic amines, such as ethyldiisopropylamine, triethylamine, picoline, pyridines or N-methylpiperidine, or amides, such as sodium amide or lithium diisopropylamide, or lithium N-silylalkylamides, such as, for example, lithium N-(bis)triphenylsilylamide, or lithium alkyls, such as n-butyllithium.

The base is employed in an amount of 1 mol to 10 mol, preferably 1 mol to 3 mol, per mole of the compounds of the general formulae (IV), (V), (VI) and (VIIa).

All the reactions are in general carried out under normal, increased or reduced pressure (for example 0.5 to 5 bar). The reactions are in general carried out under normal pressure.

Process [F] is preferably carried out in xylene or dichlorobenzene, if appropriate in the presence of triethylamine, under reflux.

The base-catalyzed transesterification is carried out with one of the abovementioned alcohols, preferably methanol, in a temperature range from −10° C. to +40° C., preferably at room temperature.

Suitable bases are in general sodium bicarbonate, sodium methanolate, hydrazine hydrate, potassium carbonate or caesium carbonate. Caesium carbonate is preferred.

Process [G] is carried out in one of the abovementioned ethers with lithium-alkyl compounds or lithium N-silylamides, such as, for example, n-butyllithium, lithium diisopropylamide or lithium bistrimethylsilylamide, preferably in tetrahydrofuran with lithium bistrimethylsilylamide or n-butyllithium, in a temperature range from −100° C. to +20° C., preferably from −75° C. to −40° C.

For process [H], the abovementioned alcohols are preferably suitable for the first step, and tetrahydrofuran is preferably suitable in the case of the subsequent cyclization. Suitable bases for the cyclization are, preferably, the abovementioned lithium N-silylalkyl compounds or n-butyllithium. n-Butyllithium is particularly preferred.

The first reaction step is carried out at the boiling point of the corresponding alcohol and the cyclization is carried out in a temperature range from −70° C. to room temperature.

The cyclization [I] is carried out in the presence of an auxiliary and/or in the presence of an acid.

Suitable acids are, in general, inorganic acids, such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or aryl radicals, for example methanesulphonic acid, ethanesulphonic acid, benzenesulphonic acid or toluenesulphonic acid. Hydrochloric acid is particularly preferred.

The acid is employed in an amount of 1 mol to 10 mol, preferably 1 mol to 2 mol, per mole of the compounds of the general formula (VIII).

Suitable auxiliaries are the customary reagents, such as phosgene, carbonyldiimidazole or diethyl carbonate or trichloromethyl chloroformate. Carbonyldiimidazole, diethyl carbonate or trichloromethyl chloroformate are preferred.

Suitable solvents are the abovementioned halogenohydrocarbons. Methylene chloride is preferred.

The cyclizations are in general carried out in a temperature range from −20° C. to 100° C., preferably at −20° C. to room temperature.

The compounds of the general formula (VI) are known or can be prepared by customary methods.

The compounds of the general formula (VIII) and (IX) are known in some cases or are new, and can then be prepared by known methods or as described above.

The compounds of the general formula (IV) are known in some cases or new and can then be prepared, for example, by reacting the corresponding amines with trichloroethyl chloroformate in one of the abovementioned solvents, preferably xylene, at the reflux temperature.

The compounds of the general formula (V) are known in some cases or new and can then be prepared, for example, starting from the corresponding carboxylic acids, by reaction either with isobutyl chloroformate/acetone, sodium azide/water or with diphenylphosphorylazide/tetrahydrofuran or with xylene or methylene chloride in the presence of one of the abovementioned bases, preferably triethylamine, at −10° C. to room temperature.

The compounds of the general formulae (VII) and (VIIa) are known in some cases or new and can be prepared either by splitting off nitrogen from the corresponding carboxylic acid azides and reaction with the corresponding alcohols or by reaction of the corresponding amines with chloroformic esters, preferably benzyl chloroformate, in one of the abovementioned solvents, preferably tetrahydrofuran or dioxane, in a temperature range from −10° C. to 200° C., preferably from 0° C. to 150° C.

The compounds of the general formula (III) are known or can be prepared by customary methods.

The compounds of the general formula (Ia), (Ib), (Ic) and (Id) are new and can be prepared as described above.

The MIC values were determined with the aid of the microdilution method in BH medium. Each test substance was dissolved in the nutrient medium. A concentration series of the test substances was prepared in the microtiter plate by serial dilution. Overnight cultures of the pathogens, which were first diluted 1:250 in the nutrient medium, were used for the inoculation. 100 μl portions of inoculation solution were added to 100 μl of the dilute nutrient solutions containing the active compound.

The microtiter plates were incubated at 37° C. and read off after about 20 hours. The MIC value (μg/ml) indicates the lowest concentration of active compound at which no growth was detectable.

The minimum inhibitory concentrations (MIC) were determined by the series dilution method on Iso-Sensitest agar (Oxoid). A series of agar plates which contained concentrations of the active compound which decreased by two-fold dilution each time was prepared for each test substance. The agar plates were inoculated with a multipoint inoculator (Denley). Overnight cultures of the pathogens which had been diluted beforehand such that each inoculation point contained about $10^4$ colony-forming particles were used for the inoculation. The inoculated agar plates were incubated at 37° C. and the germ growth was read off up to about 20 hours. The MIC value (μg/ml) indicates the lowest concentration of active compound at which no growth was detectable with the naked eye.

| MIC values (μg/ml): | | | | | | |
| --- | --- | --- | --- | --- | --- | --- |
| Ex. No. | Staph. 133 | Staph. 48N | Staph 25701 | Staph. 9TV | E. coli Neumann | Klebs. 57 USA | Psdm. Bonn |
| 24 | 2 | 1 | 0.25 | 0.25 | >64 | >64 | >64 |
| 25 | 2 | 1 | 1 | 1 | >64 | >64 | >64 |
| 26 | 2 | 1 | 1 | 1 | >64 | >64 | >64 |
| 32 | 1 | 2 | 1 | 0.5 | >64 | >64 | >64 |
| 33 | 4 | 2 | 2 | 4 | >64 | >64 | >64 |
| 36 | 4 | 4 | 4 | 2 | >64 | >64 | >64 |
| 37 | 2 | 2 | 1 | 1 | >64 | >64 | >64 |

The compounds of the general formulae (I), (Ia), (Ib), (Ic) and (Id) according to the invention display a broad antibacterial spectrum, specifically against Gram-positive bacteria, as well as Mycobacteria, Corynebacteria, Haemophilus influenzae and anaerobic germs, coupled with a low toxicity. These properties enable them to be used as chemotherapeutic active compounds in human and veterinary medicine.

The compounds according to the invention are active against a broad spectrum of microorganisms. Gram-positive bacteria and bacteria-like microorganisms, such as Mycoplasma, can be combated and the illnesses caused by these pathogens can be prevented, alleviated and/or cured with the aid of these compounds.

The compounds according to the invention are particularly active against bacteria and bacteria-like microorganisms. They are therefore particularly suitable in human and veterinary medicine for the prophylaxis and chemotherapy of local and systemic infections caused by such pathogens.

The present invention includes pharmaceutical formulations which, in addition to non-toxic, inert pharmaceutically suitable carders, comprise one or more compounds according to the invention, or which consist of one or more active compounds according to the invention, and to processes for the preparation of these compounds.

The active compound or compounds can also be in microencapsulated form, if appropriate in one or more of the abovementioned carriers.

The therapeutically active compounds should preferably be present in the abovementioned pharmaceutical formulations in a concentration of about 0.1 to 99.5, preferably about 0.5 to 95% by weight Of the total mixture.

In addition to the compounds according to the invention, the abovementioned pharmaceutical formulations can also comprise other pharmaceutical active compounds.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably comprises the active compound or compounds according to the invention in amounts of about 1 to about 80, in particular 3 to 30 mg/kg of body weight.

The new compounds can be combined in the customary concentrations and formulations together with the feed or lactamase inhibitors, for example with penicillins which are particularly resistant to penicillinase, and clavulanic acid. Such a combination would be, for example, that with oxacillin or dicloxacillin.

The compounds according to the invention can also be combined with other antibiotics for the purpose of extending the action spectrum and in order to achieve an increase in action.

Appendix to the experimental part

List of the mobile phase mixtures used for the chromatography:

| | |
|---|---|
| I | methylene chloride:methanol |
| II | toluene:ethyl acetate |
| III | acetonitrile:water |
| IV | ethyl acetate |
| V | petroleum ether:ethyl acetate |

Abbreviations:

| | |
|---|---|
| Z | benzloxycarbonyl |
| Boc | tert-butyloxycarbonyl |
| DMF | dimethylformamide |
| Ph | phenyl |
| Me | methyl |
| THF | tetrahydrofuran |
| CDI | carbonylimidazole |
| DCE | dichloroethane |

Starting compounds

EXAMPLE I

2-Benzylthio-6-isocyanato-benzo[4,5-d]thiazole hydrochloride

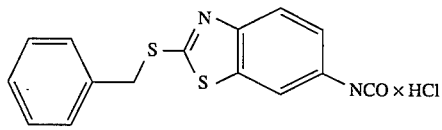

23.0 ml (0.19 mol) of trichloroethyl chloroformate are added dropwise at the boiling point to a stirred suspension of 26.05 g (0.096 mol) of 6-amino-2-benzylthiobenzo[4,5-d]-thiazole in 250 ml of 1,2-dichloroethane. After the addition, the mixture is boiled under reflux for 0.5 hours, whereupon a clear solution forms, and the mixture is then allowed to cool to room temperature. The reaction mixture is concentrated on a rotary evaporator and the oil which remains is dried under a high vacuum. 21.5 g (67%) of the title compound are obtained as a waxy solid.

Melting point: 54° C.

$R_f$=about 0.4 (toluene:ethyl acetate 4:1)

MS (DCI, $NH_3$) m/z=299 (M+H)$^+$ $^1$H-NMR (250 MHz, $D_6$-DMSO): δ=4.65 (s, 2H, $CH_2$); 7.3 (m, 5H, PH);7.5 (m, 2H); 7.85 (d, J=9 Hz, 1H).

As described for Example I, the hydrochlorides of the following isocyanates are obtained from the corresponding heteroaromatic amines by reaction with trichloromethyl chloroformate:

TABLE I

D—N=C=O × HCl

| Ex. No. | D | Yield (% of theory) | Melting point (°C.) | MS m/z = (M)+ |
|---|---|---|---|---|
| II | 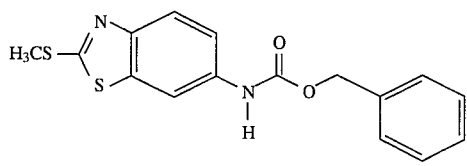 | 47 | 211 | 247 |

EXAMPLE III

6-Benzyloxycarbonylamino-2-methylthio-benzo[4,5-d]thiazole 14.80 ml (100.40 mmol) of benzyl chloroformate are added dropwise to a stirred solution, cooled to 0° C., of 17.92 g (91.30 mmol) of 6-amino-2-methylthiobenzo[4,5-d]thiazole in 240 ml of water and 60 ml of THF in the course of 30 minutes, a pH of 10 being maintained by simultaneous addition of a 4N NaOH solution. The mixture is subsequently stirred at 0° C. for a further 0.5 hour, the THF is evaporated off in vacuo and the precipitated formed is separated off by filtration, stirred thoroughly with 150 ml of pentane and dried under a high vacuum. 28.96 g (96%) of the title compound are obtained as crystals.

Melting point: 111° C.

$R_f$=0.71 (toluene:ethyl acetate 1:4)

MS (DCI, $NH_3$) m/z =331 (M+H)+

$^1$H-NMR (200 MHz, $D_6$-DMSO): δ=2.76 (s, 3H, $CH_3S$); 5.18 (m, 2H, $CH_2$); 7.4 (m, 6H, Ph, H-5); 7.77 (d, J=10 Hz, 1H, H-4); 8.18 (d, J=1.5 Hz, 1H, H-7); 10.03 (bs, 1H, NH).

As described for Example III, the compounds listed in Table II are obtained from the corresponding heteroaromatics by reaction with benzyl chloroformate:

TABLE II

| Ex. No. | D | Yield [% of theory] | Melting point: [°C.] | $R_f$/mobile phase (ratio) |
|---|---|---|---|---|
| IV | H₃C—(benzoxazole) | 99 | 74 | 0.53 II (1:4) |
| V | H₃C—(benzothiazole) | 98 | 108 | 0.55 II (2:3) |
| VI | C₆H₅—O₂S—(benzothiazole) | 96 | 146 | 0.73 II (1:4) |
| VII | (styryl)-(benzothiazole) | 83 | 164 | 0.65 I (9:1) |
| VIII | (phenyl)-(benzoxazole) | 100 | — | 0.70 II (1:1) |

TABLE II-continued

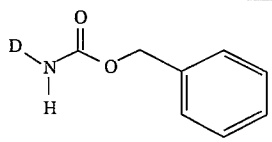

| Ex. No. | D | Yield [% of theory] | Melting point: [°C.] | R_f/mobile phase (ratio) |
| --- | --- | --- | --- | --- |
| IX | 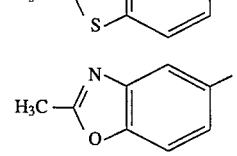 | 95 | — | 0.53 II (1:1) |
| X | 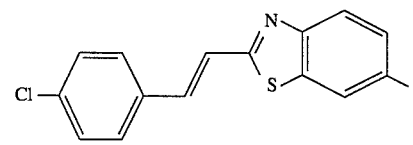 | 94 | — | 0.50 II (1:1) |
| XI | | 90 | 190 | 0.84 II (1:2) |

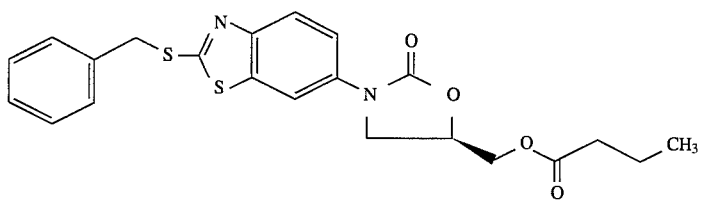

EXAMPLE XII (5R)-3-(2-Benzylthio-benzo[4,5-d]thiazol-6-yl)-5-butyryloxy-methyl-oxazolidin-2-one A suspension of 333 mg (3.84 mmol) of lithium bromide and 838 mg (3.84 mmol) of tributylphosphine oxide in 200 ml of xylene is boiled for 1 hour using a water separator. A mixture of 8.0 ml (57.6 mmol) of triethylamine and 10.0 ml (70.40 mmol) of (R)-glycidyl butyrate is added dropwise at the boiling point. At the same time, a solution of 21.0 g (63 mmol) of the compound from Example I in 200 ml of xylene is added dropwise in the come of 20 minutes. When the addition has ended, the mixture is subsequently stirred under reflux for a further 5 minutes. It is allowed to cool to room temperature and the solvent is evaporated off in vacuo. Chromatography of the residue over 0.5 kg of silica gel (toluene:ethyl acetate 4:1 ) gives 16.2 g (57%) of the title compound as pale crystals.

Melting point: 109° C.

R_f=0.32 (toluene:ethyl acetate 4:1)

MS (FAB) m/z=443 (M+H)⁺

$^1$H-NMR (200 MHz, D_6-DMSO): δ=0.82 (t, J=7 Hz, 3H, CH_3CH_2); 1.5 (m, 2H, CH_3CH_2CH_2CO); 2.30 (t,J=7 Hz, 2H, CH_3CH_2CH_2CO); 3.89 (dd, J=7 Hz, 10 Hz, 1H, H-4 trans); 4.23 (dd, J=9 Hz, 10 Hz, 1H, H-4 cis); 4.33 (m, 2H, CH_2O); 4.62 (s, 2H, PhCH_2S); 4.97 (m, 1H, H-5); 7.35 (m, 3H, Ph); 7.5 (m, 2H, Ph); 7.75 (dd, J=1.5, 10 Hz, 1H, benzothiazole-H-5); 7.90 (d, J=10 Hz, 1H, benzothiazole-H-4); 8.15 (d, J=1.5 Hz, 1H, benzothiazole-H-7).

EXAMPLE XIII (5R)-3-(2-Methylthio-benzo[4,5-d]thiazol-6-yl)-5-hydroxymethyl-oxazolidin-2-one

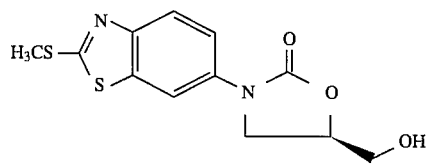

35.00 ml (87.64 mmol) of a 2.5M solution of n-butyllithium in n-hexane are slowly added to a stirred solution, cooled to −78° C., of 28.90 g (87.64 mmol) of 6-benzyloxy-carbonylamino-2-methylthio-benzo[4,5-d]thiazole (Example III) and 1 mg of 1,10-phenanthroline hydrate in 280 ml of anhydrous THF until the colour changes. Thereafter, 12.40 g (87.64 mmol) of (R)-glycidyl butyrate are added dropwise and the reaction mixture is allowed to warm to room temperature in the course of 16 hours. 200 ml of saturated aqueous NH_4Cl solution are then added dropwise in the course of 15 minutes. The aqueous phase is extracted with 3×100 ml of ethyl acetate and the organic phases are combined, washed with 2×100 ml of NaCl solution and dried over MgSO_4. After the solvent has been evaporated off in vacuo and the residue has been titrated with ether, 17.25 g (67%) of the title compound are obtained as colourless crystals.

Melting point: 156° C.
$R_f$=0.24 (toluene:ethyl acetate 1:4)
MS (DCI, $NH_3$) m/z=297 $(M+H)^+$
$^1$H-NMR (200 MHz, $D_6$-DMSO): δ=2.78 (s, 3H, $SCH_3$); 3.6–3.8 (m, 2H, $CH_2O$); 3.90 (dd, J=7, 10 Hz, 1H, H-4 trans); 4.15 (dd, J=10, 10 Hz, 1H, H-4 cis); 4.72 (m, 1H, H-5); 5.25 (t, J=6 Hz, 1H, OH); 7.74 (dd, J=1.5, 10 Hz, 1H, benzothiazole H-5); 7.87 (d, J=10 Hz 1H, benzothiazole H-4); 8.18 (d, J=1.5 Hz, 1H, benzothiazole H-7).

EXAMPLE XIV (5R)-3-(2-Benzylthio-benzo[4,5-d]thiazol-6-yl)-5-hydroxymethyl-oxazolidin-2-one

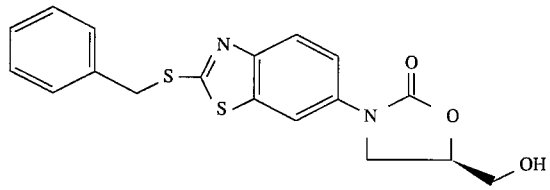

12 mg (0.367 mmol) of caesium carbonate are added to a solution of 16.15 g (36.49 mmol) of the compound from Example XII in 150 ml of anhydrous methanol and the mixture is stirred at room temperature for 18 hours. The solvent is evaporated off in vacuo and the residue is stirred with 30 ml of ether. The precipitate is separated off by filtration, washed with 25 ml of water and 5 ml of ether and dried under a high vacuum. 13.01 g (96%) of the title compound are obtained as pale crystals.

Melting point: 145° C.
$R_f$=0.06 (toluene:ethyl acetate 7:3)
MS (DCI, $NH_3$) m/z=373 $(M+H)^+$
$^1$H-NMR (200 MHz, $D_6$-DMSO): δ=3.50–3.75 (m, 2H, $CH_2O$); 3.89 (dd, J=7, 10 Hz, 1H, H-4 trans); 4.13 (dd, J=10, 10 Hz, 1H, H-4 cis); 4.63 (s, 2H, $CH_2$); 4.70 (m, 1H, H-5); 5.25 (t, J=6 Hz, 1H, OH); 7.30 (m, 3H, Ph); 7.50 (m, 2H, Ph); 7.77 (dd, J=1.5, 10 Hz, 1H, benzothiazole H-5); 7.89 (d, J=10 Hz, 1H, benzothiazole H-4); 8.18 (d, J=1.5 Hz, 1H, benzothiazole H-7).

The compounds listed in Table III are prepared analogously to the instructions of Examples XII–XIV:

TABLE III

| Ex. No. | D | Analogously to preparation method (Reagent) | Yield [% of theory] | Melting point. [°C.] | $R_f$/ mobile phase (ratio) | $[α]_D^{20}$ (DMSO) | MS (FAB) m/z $(M + H)^+$ |
|---|---|---|---|---|---|---|---|
| XV | N=C(CH₃)O-aryl | XIII (n-BuLi) | 80 | 188 | 0.13, II (1:4) | | 249 |
| XVI | N=C(C₆H₅)O-aryl | XIII (n-BuLi) | 78 | 208 | 0.10, II (1:1) | −44.1 (c = 1) | 310[a)] |
| XVII | N=C(CH₃)S-aryl | XIII (n-BuLi) | 71 | 164 | 0.12, II (1:4) | | 265 |
| XVIII | N=C(CH=CH-C₆H₅)S-aryl | XIII (n-BuLi) | 76 | 188 | 0.52, I (9:1) | | 352[a)] |
| XIX | N=C(CH₃)S-aryl | XIII (n-BuLi) | 57 | | 0.05, II (1:1) | | — |

TABLE III-continued

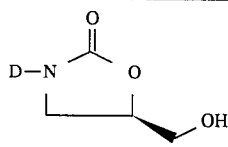

| Ex. No. | D | Analogously to preparation method (Reagent) | Yield [% of theory] | Melting point. [°C.] | $R_f$/ mobile phase (ratio) | $[\alpha]_D^{20}$ (DMSO) | MS (FAB) m/z $(M + H)^+$ |
|---|---|---|---|---|---|---|---|
| XX | (2-methylphenyl C(CH₃)=N-O structure) | XIII (n-BuLi) | 68 | | 0.47, II (1:1) | −52.3 (c = 1) | 248[a] |
| XXI | (2-methylphenyl C(C₆H₅)=N-O structure) | XIII (n-BuLi) | 78 | 208 | 0.10, II (1:1) | −44,2 (c = 1) | 310[a] |
| XXII | (4-Cl-phenyl-CH=CH-benzothiazole-methyl structure) | XIII (n-BuLi) | 72 | 203 | 0.18, II (1:2) | — | 387[b] |

[a] MS (EI) m/z = M⁺
[b] MS (DCI/NH₃) m/z = (M + H)⁺

EXAMPLE XXIII

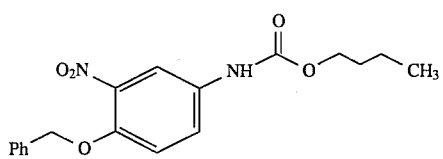

4-Benzyloxy-1-butyloxycarbonylamino-3-nitrobenzene 12.4 ml (93.6 mmol) of butyl chloroformate in 80 ml of acetone are added to a solution of 24.3 g of 3-nitro4-benzyloxybenzoic acid (J. Med. Chem. 1967 (10) 462) and 8.7 g (86.4 mmol) of triethylamine in 200 ml of acetone at 0° C. The mixture was stirred at −5° C. for a further hour, 7.0 g (108 mmol) of sodium azide in 100 ml of water are then added dropwise and the mixture is stirred at 0° C. for 2 hours. The mixture is subsequently introduced onto 800 ml of ice-water and the precipitate which has separated out is filtered off with suction and then introduced into 300 ml of boiling n-butanol.

When the addition has ended, the mixture is stirred under reflux for a further 10 minutes and cooled and the precipitate which has separated out is filtered off.

Yield: 23.0 g (75%)
Melting point: 121°–122° C.

$^1$H-NMR (250 MHz, D₆-DMSO): δ9.8 (bs, 1H), 8.12 (d, 1H), 7.62 (dd, 1H), 7.20–7.45 (m, 6H), 5.25 (s, 2H), 4.10 (t, 2H), 1.70 (m, 2H), 1.40 (m, 2H), 0.48 (t, 3H).

The compounds listed in Table IV are prepared analogously to the instructions of Example XXIII:

TABLE IV

| Ex. No. | Compound | Yield (% of theory) | Melting point (°C.) | $R_f$ mobile phase (ratio) | MS (DCI, NH₃) m/z $(M + H)^+$ |
|---|---|---|---|---|---|
| XXIV |  | 63 | 133 | 0.51 (VII, 95:5) | 345 |

EXAMPLE XXV (5R)-3-(4-Benzyloxy-3-nitrophenyl)-5-(hydroxymethyl)-oxazolidin-2-one

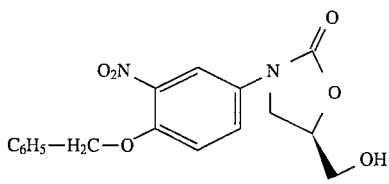

23.0 g (66.7 mmol) of the compound from Example XXIII are dissolved in 200 ml of THF and the solution is cooled to 0° C. About 68 ml of 1.0M LiHMDS solution in THF are now slowly added dropwise. 9.5 ml (68 mmol) of (R)-glycidyl butyrate are then added dropwise. The mixture is allowed to come to room temperature, saturated ammonium chloride solution is added and the THF is stripped off in vacuo. The resulting precipitate is filtered off with suction, washed with water and ether and dried under a high vacuum.

Yield: 20.85 g (91%)
Melting point: 128°–130° C.
$R_f$=(II, 1:1)=0.21
MS (FAB): m/z=345M⊕

The compounds listed in Table V are prepared analogously to the instructions of

EXAMPLE XXV:

Melting point: 149°–150° C.
$R_f$=(VII, 5:1)=0.36
MS (FAB): m/z=423
$^1$H-NMR ([D$_6$]DMSO): δ=8.12 (d, J=1 Hz, 1H, Ph); 7.75 (dd, J=6 Hz. J=1 Hz 1H, Ph); 7.35–7.55 (m, 6H, Ph); 5.30 (s, 2H, CH$_2$); 4.40–4.60 (m, 2H, CH$_2$O); 4.22 (t, J=9 Hz 1H), 4-H); 3.85 (dd, J=9 Hz, J=5 Hz, 1H, 4-H); 3.25 (s, 3H, SO$_2$CH$_3$).

The compounds listed in Table VI are prepared analogously to the instructions of Example XXVII:

TABLE V

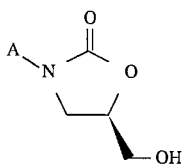

| Ex. No. | A | Yield (% of theory) | Melting point. (°C.) | $R_f$ mobile phase (ratio) | $(α)_D^{20}$ (DMSO) | MS (FAB) m/z (M$^+$ + H) |
|---|---|---|---|---|---|---|
| XXVI | O$_2$N—⌬—O—CH$_2$—C$_6$H$_5$ | 73 | 137–139 | 0.28 (II, 1:1) | −38.1 (c = 0.985) | 345 |

EXAMPLE XXVII (5R)-3-(4-Benzyloxy-3-nitrophenyl)-5-(methylsulphonyloxymethyl)-oxazolidin-2-one

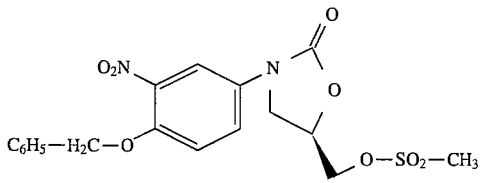

23.6 ml (230 mmol) of methanesulphonyl chloride are slowly added to a solution, cooled to 0° C., of 71.5 g (208 mmol) of the compound from Example XXV and 35 ml (250 mmol) of triethylamine in 650 ml of anhydrous THF. The resulting precipitate is filtered off with suction, washed with water and toluene and dried under a high vacuum.

Yield: 65.8 g (75%)

TABLE VI

[Structure: oxazolidinone with A-N, and -O-SO₂-CH₃ substituent]

| Ex. No. | A | Yield (% of theory) | Melting point. (°C.) | R_f mobile phase (ratio) | $(\alpha)_D^{20}$ (DMSO) | MS (FAB) m/z (M⁺ + H) |
|---|---|---|---|---|---|---|
| XXVIII | 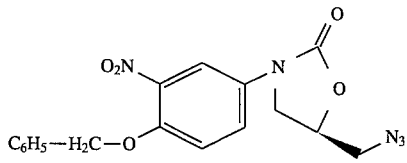 | 92 | 140–142 | 0.34 (VII, 5:1) | −48.8 (c = 1.01) | 423 |

EXAMPLE XXIX (5R)-3-(4-Benzyloxy-3-nitrophenyl)-5-(azidomethyl)-oxazolidin-2-one

[Structure of azide compound]

4.4 ml (66.9 mmol) of sodium azide are added to a solution of 25.7 g (60.8 mmol) of the compound from Example XXVII in 200 ml of anhydrous DMF and the mixture is stirred at 70° C. for 12 hours. It is allowed to cool to room temperature and 200 ml of ice-water are stirred in. The resulting precipitate is filtered off, washed with water and petroleum ether and dried in vacuo.

Yield: 21.4 g (95%)
Melting point: 158°–160° C.
$R_f$=0.48
MS (EI): m/z=370M⊕
¹H-NMR ([D₆]DMSO: δ=8.05 (d, 1H, J=8 Hz, Ph); 7.25–7.50 (m, 7H, Ph); 5.30 (s, 2H, CH₂); 4.85–5.05 (m, 1H, 5-H); 4.23 (t, J=9 Hz, 1H, 4-H); 3.55–3.90 (m, 3H, 4-H, CH₂N₃).

The compounds listed in Table VII are prepared analogously to the instructions of Example XXIX:

EXAMPLE XXXI (5S)-3-(4-Benzyloxy-3-nitrophenyl)-5-(aminomethyl)-oxazolidin-2-one

[Structure of amine compound]

A solution of 53.1 g (144 mmol) of the compound from Example XXIX in 160 ml of 1,2-dimethoxyethane is heated to 50° C. 20.4 ml (173 mmol) of trimethyl phosphite are slowly added dropwise (evolution of gas), and when the addition has ended the mixture is stirred at 90° C. for 2 hours. 36 ml of 6N HCl are now added dropwise and the mixture is stirred at 90° C. for a further 22 hours. It is allowed to cool to room temperature, 810 ml of 0.1N HCl are added, the aqueous phase is washed with ether (3×320 ml) and the pH is then brought to 9. The aqueous phase is then extracted (2×300 ml) with ethyl acetate (3×650 ml) and the combined organic phases are washed with saturated NaCl solution (1×100 ml) and dried (Na₂SO₄). The solvents are stripped off in vacuo and the residue is dried under a high vacuum.

Yield: 47.2 g (96%)
Melting point: 135°–136° C.

TABLE VII

[Structure: oxazolidinone with A-N, and -N₃ substituent]

| Ex. No. | A | Yield (% of theory) | Melting point (°C.) | R_f mobile phase (ratio) | $(\alpha)_D^{20}$ (DMSO) | MS (FAB) m/z (M⁺ + H) |
|---|---|---|---|---|---|---|
| XXX | 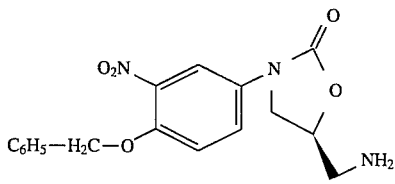 | 92 | 138–140 | 0.26 (VII, 5:1) | −119.4 (c = 1.1) | 370 |

65

$R_f$(VIII, 85:10:5)=0.05

MS (EI): m/z=344M⊕

$^1$H-NMR ([D$_6$]DMSO): δ=8.30–9.10 (bs, 3H, NH$_3$); 8.15 (d, 1H, Ph); 7.3–7.8 (m, 7H, Ph); 5.30 (m, 2H, CH$_2$); 4.90–5.10 (m, 1H, 4-H); 4.20 (m, 1H, 5-H); 4.00 (m, 1H, 5-H); 3.10–3.40 (m, 2H, CH$_2$N).

The compounds listed in Table VIII are prepared analogously to the instructions of Example XXXI:

MS (FAB): m/z=386 (M+H)$^+$ $^1$H-NMR ([D$_6$]DMSO): δ=8.24 (t, J=4 Hz, 1H, NH); 8.10 (d, J=1 Hz, 1H, Ph); 7.75 (dd, J=6 Hz, J=1 Hz, 1H, Ph); 7.20–7.50 (m, 6H, Ph); 5.30 (s, 2H, CH$_2$); 4.70–4.80 (m, 1H, 5-H); 4.15 (t, J=9 Hz 1H, 4-H); 3.70 (dd, J=9 Hz, J=5 Hz, 1H, H-4); 3.35–3.50 (m, 5H, CH$_2$N, NCH$_3$); 1.83 (s, 3H, COCH$_3$).

TABLE VIII

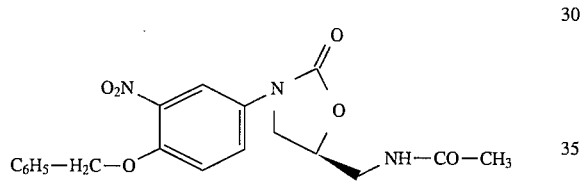

| Ex. No. | A | Yield (% of theory) | Melting point (°C.) | R$_f$ mobile phase (ratio) | MS (FAB) m/z (M$^+$) |
|---|---|---|---|---|---|
| XXXII | O$_2$N— / C$_6$H$_5$—H$_2$C—O— (phenyl) | 89 | 132–134 | 0.08 (VIII, 85:10:5) | 344 |

EXAMPLE XXXIII (5S)-3-(4-Benzyloxy-3-nitrophenyl)-5-(acetylaminomethyl)-oxazolidin-2-one O$_2$N— / C$_6$H$_5$—H$_2$C—O— (phenyl)—N(oxazolidinone)—CH$_2$—NH—CO—CH$_3$ 14.6 ml (205 mmol) of acetyl chloride are slowly added dropwise to a solution, cooled to 0° C., of 47.2 g (137 mmol) of the compound from Example XXXI and 29.4 ml (212 mmol) of triethylamine in 500 ml of anhydrous THF. The mixture is subsequently stirred at 0° C. for 2 hours and poured onto ice-water. The precipitate is filtered off with suction, washed with water and ether and dried under a high vacuum over P$_2$O$_5$.

Yield: 48.9 g (93%)
Melting point: 177°–178° C.
R$_f$(VII,=0.5

The compounds listed in Table IX are prepared analogously to the instructions of Example XXXIII:

TABLE IX

| Ex.-No. | A | Yield (% of theory) | Melting point (°C.) | R$_f$ mobile phase (ratio) | (a)$_D^{20}$ (DMSO) | MS (FAB) m/z (M + H) |
|---|---|---|---|---|---|---|
| XXXIV | H$_2$N— / C$_6$H$_5$—H$_2$C—O— (phenyl) | 86 | 155–156 | 0.62 (VII, 1:1) | −23.6 (c = 1.05) | 386 |

EXAMPLE XXXV (5S)-3-(3-Amino-4-hydroxyphenyl)-5-(aminomethyl)-oxazolidin-2-one

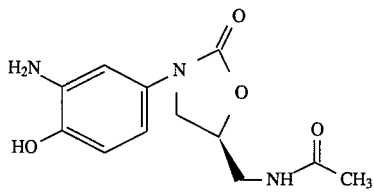

3.58 g (9.28 mmol) of the compound from Example XXXIII and 350 mg of Pd—C (10%) are stirred in 100 ml of methanol and 100 ml of THF under hydrogen (1 atmosphere) for 3 hours. The catalyst is filtered off, the solvent is stripped off and the residue is dried.

Yield: 2.5 g (quantitative)

$R_f$(VII, 1:1)=0.42

MS (CI): m/z=265 (M$^+$)

$[\alpha]_D^{20}$=−110.45(c=1.0, DMSO)

$^1$H-NMR ([D$_6$]DMSO): δ=9.0–9.5 (bs, 1H, OH); 8.20 (t, J=4 Hz, 1H, NHCO); 7.05 (bs, 1H, Ph); 6.55 (bs, 2H, Ph); 4.55–4.70 (m, 1H, 5-H); 4.30–4.52 (bs, 2H, NH$_2$); 3.95 (t, J=6 Hz, 1H, 4-H); 3.60 (dd, J=7 Hz, J=4 Hz, 1H, 4-H); 3.40 (t, J=4 Hz, 2H, CH$_2$N); 1.73 (s, 3H, COCH$_3$).

As described for Example XXXV, the compounds listed in Table X are obtained from the corresponding starting compounds:

ice-water. The organic phase is separated off, washed with 20 ml of saturated NaHCO$_3$ solution and 20 ml of ice-water and dried over MgSO4. The solvent is evaporated off in vacuo and the residue is stirred with 50 ml of ether, filtered off with suction and dried under a high vacuum. 14.17 g (82%) of the title compound are obtained as colourless crystals.

Melting point: 106° C.

$R_f$=0.41 (methylene chloride:methanol 95:5)

MS (DCI, NH$_3$) m/z=375 (M+H)$^+$ $^1$H-NMR (250 MHz, D$_6$-DMSO): δ=2.80 (s, 3H, CH$_3$S); 3.28 (s, 3H, OSO$_2$CH$_3$); 3.90 (dd, J=7, 10 Hz, 1H, H-4 trans); 4.27 (dd, J=10, 10 Hz, 1H, H-4 cis); 4.55 (m, 2H, CH$_2$O); 5.04 (m, 1H, H-5); 7.72 (dd, J=1.5, 10 Hz, 1H, benzothiazole H-5); 7.88 (d, J=10 Hz, 1H, benzothiazole H-4); 8.19 (d, J=1.5 Hz, 1H, benzothiazole H-7).

As described for Example 1, the following methanesulphonates are obtained from the corresponding alcohols (Table 1):

TABLE X

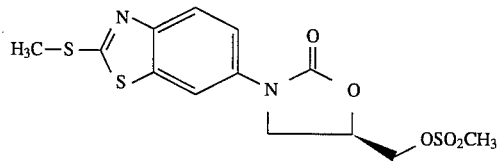

| Ex. No. | A | Yield (%) of theory | Melting point. (°C.) | $R_f$ mobile phase (ratio) | $(\alpha)_D^{20}$ (DMSO) | MS (CDl, NH$_3$) m/z (M + H)$^+$ |
|---|---|---|---|---|---|---|
| XXXVI | H$_2$N— / HO— (aryl) | quant. | 221–222 | 0.31 (VII, 1:1) | −19.89 (c = 1.0) | 265 |

PREPARATION EXAMPLES

Example 1

(5R)-3-(2-Methylthio-benzo[4,5-d]thiazol-6-yl)-5-methanesulphonyloxymethyloxazolidin-2-one 4.60 ml (59.78 mmol) of methanesulphonyl chloride are slowly added to a stirred solution, cooled to 0° 71346 C., of 13.63 g (45.99 mmol) of the compound from Example XIII and 9.00 ml (64.39 mmol) of triethylamine in 90 ml of anhydrous methylene chloride. The mixture is subsequently stirred at 0–5° C. for 15 minutes and stirred into 100 ml of

TABLE 1

![structure: D-N-C(=O)-O-CH(CH2)-OSO2CH3 oxazolidinone with mesylate]

| Ex. No. | D | Yield [% of theory] | Melting point [°C.] | $R_f$/mobile phase (ratio) | $[\alpha]_D^{20}$ (DMSO) | MS (FAB) m/z (M + H)+ |
|---|---|---|---|---|---|---|
| 2 | H3C-C(=N-Ar)-O (Ar = phenyl) | 69 | 159 | 0.26, I (95:5) | | 327 |
| 3 | C6H5-C(=N-Ar)-O | 94 | | 0.20, II (1:1) | −55.5° (c = 1) | 389 |
| 4 | H3C-C(=N-Ar)-S | 73 | 162 | 0.28, I (95:5) | | 343 |
| 5 | C6H5-CH2-S-C(=N-Ar)-S | 87 | 131 | 0.47, I (95:5) | | 451 |
| 6 | C6H5-CH=CH-C(=N-Ar)-S | 75 | 146 | 0.53, IV | | 431 |
| 7 | H3C-C(=N-Ar)-S (isomer) | 59 | | 0.29, II (1:5) | | |
| 8 | H3C-C(=N-Ar)-O (isomer) | 88 | | 0.58[b)] (5:1) | −52.3° (c = 1) | 327 |

[b)] toluene:ethanol

Example 9

(5R)-3-(2-Methylthio-benzo[4,5-d]thiazol-6-yl)-5-azidomethyl-oxazolidin-2-one

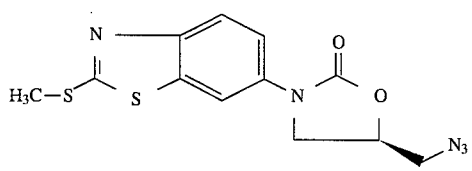

3.20 g (49.16 mmol) of sodium azide are added to a stirred solution of 14.16 g (37.81 mmol) of the compound from Example 1 in 50 ml of anhydrous DMF and the mixture is stirred at 70° C. for 3 hours. H is allowed to cool to room temperature and stirred into 100 ml of ice-water. The resulting precipitate is separated off by filtration, washed with 50 ml of water and 20 ml of petroleum ether and dried in air. 11.60 g (95%) of the title compound are obtained as pale crystals.

Melting point: 136° C.
$R_f$=0.59 (methylene chloride:methanol 95:5)
MS (DCI, NH$_3$)m/z=322 (M+H)+
$^1$H-NMR (250 MHz, D$_6$-DMSO): δ=2.79 (s, 3H, CH$_3$S); 3.76 (m, 2H, CH$_2$N$_3$); 3.87 (dd, J=6.9 Hz 1H, H-4 trans); 4.21 (dd, J=9.9 Hz, 1H, H-4 cis); 4.92 (m, 1H, H-5); 7.73 (dd, J=1, 9 Hz 1H, benzothiazole H-5); 7.87 (d, J=9 Hz, 1H, benzothiazole H-4); 8.18 (d, J=1 Hz, 1H, benzothiazole H-7).

As described for Example 9, the following azides are obtained from the corresponding methanesulphonates (Table 2):

TABLE 2

$$\text{D—N} \underset{\underset{\diagdown N_3}{\diagup}}{\overset{\overset{O}{\|}}{\diagdown}} O$$

| Ex. no. | D | Yield [% of theory] | Melting point. [°C.] | R_f/mobile phase (ratio) | $[\alpha]_D^{20}$ (DMSO) | MS (FAB) m/z (M + H)+ |
|---|---|---|---|---|---|---|
| 10 | 2-methyl-benzoxazol-5-yl (N=C(CH₃)–O aryl) | 94 | 111 | 0.42, I (95:5) | | 274 |
| 11 | 2-phenyl-benzoxazol-5-yl (N=C(C₆H₅)–O aryl) | 97 | | 0.34, II (1:1) | −128.5° (c = 1) | 335[a] |
| 12 | 2-methyl-benzothiazol-5-yl (N=C(CH₃)–S aryl) | 90 | 79 | 0.51, I (95:5) | | 280 |
| 13 | 2-(benzylthio)-benzothiazol-5-yl (C₆H₅CH₂S–C(=N)–S aryl) | 97 | 110 | 0.34, II (4:1) | | 398 |
| 14 | 2-styryl-benzothiazol-5-yl (C₆H₅–CH=CH–C(=N)–S aryl) | 90 | 144 | 0.48, IV | | 377[a] |
| 15 | 2-methyl-benzothiazol-6-yl (N=C(CH₃)–S aryl) | 98 | | 0.43, II (1:1) | | |
| 16 | 2-methyl-benzoxazol-6-yl (N=C(CH₃)–O aryl) | 79 | | 0.45 | −129.7° (C = 0.5) | 273[a] |

[a] MS (EI) m/z = (M)+

Example 17

(5S)-3-(2-Methylthio-benzo[4,5-d]thiazol-6-yl)-5-aminomethyl-oxazolidin-2-one hydrochloride

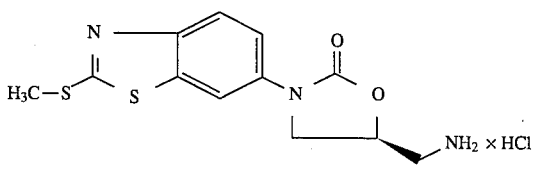

A stirred solution of 11.58 g (36.03 mmol) of the compound from Example 9 in 25 ml of 1,2-dimethoxyethane is heated to 50° C. 5.00 ml (43.24 mmol) of trimethyl phosphite are slowly added dropwise (evolution of gas), and when the addition has ended the mixture is subsequently stirred at 90° C. for 2 hours. 7.2 ml of 6N HCl are then added dropwise and the mixture is subsequently stirred at 90° C. for a further 3 hours. It is allowed to cool to room temperature and the precipitate is separated off by filtration, washed with 2×10 ml of 1,2-dimethoxyethane and dried under a high vacuum over NaOH. 9.94 g (83%) of the title compound are obtained as a colourless solid.

Melting point: 110° C.

R_f=0.09 (acetonitrile:water 9:1 )

¹H-NMR (250 MHz, D₆-DMSO): δ=2.80 (s, 3H, CH₃S); 3.28 (m, 2H, CH₂NH₂); 3.98 (dd, J 7, 9 Hz, 1H, H-4 trans); 4.28 (dd, J=9, 9 Hz, 1H, H-4 cis); 5.02 (m 1H, H-5); 7.70 (dd, J=1, 10 Hz, 1H, benzothiazole H-5); 7.89 (d, J=10 Hz, 1H, benzothiazole H-4); 8.18 (d, J=1 Hz, 1H, benzothiazole H-7).

As described for Example 17, the following products are obtained by reaction of the corresponding azides (Table 3):

TABLE 3

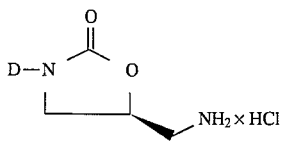

| Ex. No. | D | Yield [% of theory] | Melting point [°C.] | R_f/mobile phase (ratio) | $[\alpha]_D^{20}$ (DMSO) | MS (FAB) m/z (M − Cl)+ |
| --- | --- | --- | --- | --- | --- | --- |
| 18 | 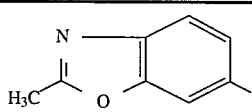 | 83 | | 0.15, III (9:1) | | 248 |
| 19 | 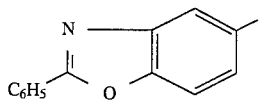 | 80 | >250 | 0.08, I (10:1) | −38.5° (c = 1.0) | 309[a] |
| 20 | 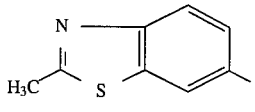 | 94 | | 0.16, III (9:1) | | 264 |
| 21 | 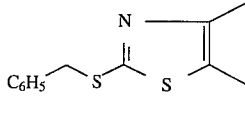 | 45 | 257 | 0.25, III (9:1) | | 372 |
| 22 | 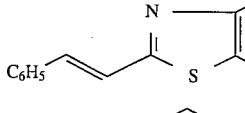 | 94 | 303 | 0.19, III (9:1) | | 351[a] |
| 23 | 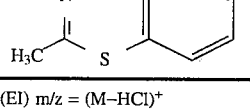 | 43 | | 0.12, I (10:1) | | |

[a] MS (EI) m/z = (M−HCl)+

Example 24

Method A (5S)-3-(2-Methylthio-benzo[4,5-d]thiazol-6-yl)-5-acetylaminomethyl-oxazolidin-2-one

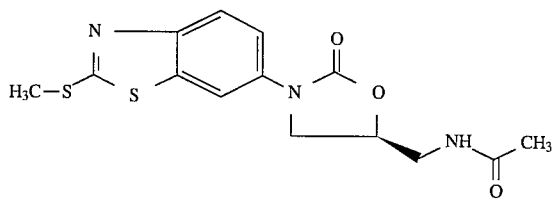

A solution of 1.24 g (30.99 mmol) of sodium hydroxide in 8 ml of water is added to a stirred solution of 9.35 g (28.17 mmol) of the compound from Example 17 in 80 ml of THF. 2.90 ml (30.99 mmol) of acetic anhydride in 3 ml of THF are slowly added dropwise at 0°–° C. and the pH is kept at 9 by simultaneous addition of a 5N aqueous NaOH solution. The mixture is subsequently stirred at 0° C. for 1 hour and the solvent is evaporated off in vacuo. The residue is stirred thoroughly with 2×20 ml of water, separated off and dried under a high vacuum over Sicapent. After recrystallization from 2-propanol, 7.88 g (83%) of the title compound are obtained as colourless crystals.

Melting point: 136° C.
R_f=0.15 (methylene chloride:methanol 95:5)
MS (DCI, NH_3) m/z=338 (M+H)+
$^1$H-NMR (200 MHz, D_6-DMSO): δ=1.84 (s, 3H, COCH_3); 2.79 (s,, 3H, CH_3S); 3.42 (t, J=6.5 Hz, 2H, CH_2N); 3.81 (dd, J=7, 10 HZ, 1H, H-4 trans); 4.19 (dd, J=10 Hz, 1H, H-4 cis); 4.75 (m, 1H, H-5); 7.72 (dd, J=1, 10 Hz, 1H, benzothiazole H-5); 7.85 (d, J=10 Hz, 1H, benzothiazole H-4); 8.15 (d, J=1 Hz, 1H, benzothiazole H-7); 8.28 (bt, J=5 Hz 1H, NH).

Example 25

Method B (5S)-3-(2-Methyl-benzo[4,5-d]oxazol-6-yl)-5-acetaminomethyl-oxazolidin-2-one

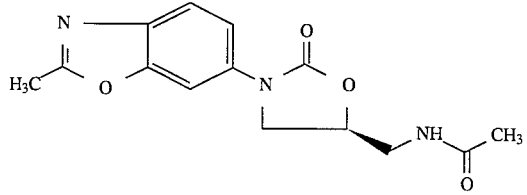

4.61 ml (67.43 mmol) of acetyl chloride are slowly added dropwise to a stirred solution, cooled to 0° C., of 13.20 g (48.51 mmol) of the compound from Example 18 and 16.90 ml (121.25 mmol) of triethylamine in 132 ml of anhydrous methylene chloride. The mixture is subsequently stirred at 0° C. for 2 hours and diluted with 200 ml of water and 150 ml of methylene chloride, the organic phase is separated off, the aqueous phase is extracted with 20 ml of methylene chloride and the combined organic extracts are dried over $MgSO_4$. After the solvent has been evaporated off in vacuo and the residue has been titrated with 150 ml of ether, 11.66 g (83%) of the title compound are obtained as colourless crystals.

Melting point: 181° C.

$R_f$=0.40 (19:1)

MS (DCI, $NH_3$): m/z=290 (M+H)⁺

¹H-NMR (300 MHz): δ1.83 (s, 3H, $COCH_3$); 2.60 (s, 2H, $CH_3$); 3.42 (t, J=7 Hz, 2H, $CH_2N$); 3.82 (dd, J=7.9 Hz, 1H, H-4 trans); 4.19 (dd, J=10, 10 Hz 1H, H-4 cis); 4.75 (m, 1H, H-5); 7.47 (dd, J=1, 9 Hz, 1H, benzoxazole H-5); 7.64 (d, J=9 Hz, 1H, benzoxazole H-6); 7.89 (d, J=1 Hz, 1H, benzoxazole H-7); 8.23 (m, 1H, NH).

As described for Example 24 and 25, the following products are obtained by acylation of the corresponding amines (Table 4):

Example 31

(5S)-3-(2,3-Dimethyl-benzo[4,5-d]-thiazol-6-yl)-5-acetylaminomethyloxazolidin-2-one

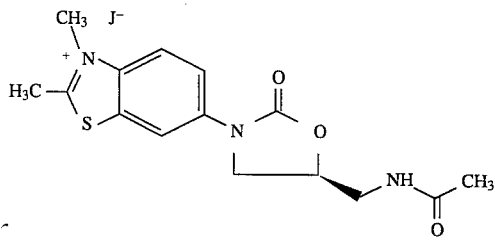

0.35 ml (5.05 mmol) of iodomethane is added to a stirred solution of 180 mg (0.59 mmol) of the compound from Example 26 in 1.5 ml of anhydrous acetonitrile and the mixture is stirred at 60° C. for 5 hours, a pale precipitate being formed. 40 ml of ether are added, the mixture is stirred thoroughly for 10 minutes and the precipitate is separated off by filtration, washed with 5 ml of ether and dried under a high vacuum. 148 mg (56%) of the title compound are obtained as pale crystals.

Melting point: 161° C. (decomposition)

$R_f$=0.06 (acetonitrile/water 4:1 )

TABLE 4

| Ex. No. | D | Analogously to preparation method | Yield [% of theory] | Melting point [°C.] | $R_f$/mobile phase (ratio) | $[\alpha]_D^{20}$ (DMSO) | MS (FAB) m/z (M + H)⁺ |
| --- | --- | --- | --- | --- | --- | --- | --- |
| 26 | H₃C-C(=N-)-S- (tolyl) | A | 69 | 133 | 0.21, I (95:5) | | 306 |
| 27 | C₆H₅-S-C(=N-)-S- (tolyl) | A | 90 | 159 | 0.56, III (9:1) | | 414 |
| 28 | C₆H₅-CH=CH-C(=N-)-S- (tolyl) | A | 86 | 213 | 0.35, I (9:1) | | 393ᵃ⁾ |
| 29 | C₆H₅-C(=N-)-O- (tolyl) | B | 22 | 225 | 0.29, I (10:1) | -20.4° (c = 1) | 351ᵃ⁾ |
| 30 | H₃C-C(=N-)-S- (tolyl) | B | 87 | 167 | 0.74, I (5:1) | | |

ᵃ⁾MS (EI) m/z = (M)⁺

MS (FAB): 320 (M+), free cation

¹H-NMR (250 MHz, $D_6$-DMSO): δ=1.85 (s, 3H, $CH_3$); 3.13 (s, 3H. $CH_3$); 3.47 (m, 2H, $CH_2N$); 3.87 (dd, J=7, 9 Hz, 1H, H-4 trans); 4.20 (s, 3H, $CH_3N$); 4.23 (dd, J=9, 9 Hz, 1H;

H-4 cis); 4.83 (m, 1H, H-5); 8.10 (dd, J=1.5, 10 Hz, 1H, benzothiazole H-5); 8.30 (m, 2H, NH, benzothiazole H-4); 8.60 (d, J=1.5 Hz, 1H, benzothiazole H-7).

Example 32

(5S)-3-(2-Methylsulphinyl-benzo[4,5-d]-thiazol-6-yl)-5-acetylaminomethyl-oxazolidin-2-one

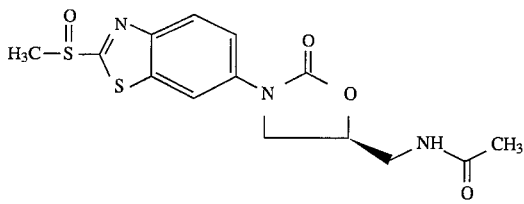

351 mg (1.63 mmol) of 80% strength m-chloroperbenzoic acid are added to a stirred solution, cooled to 0° C, of 500 mg (1.48 mmol) of the compound from Example 24 in a mixture of 6 ml of methylene chloride and 9 ml of chloroform, and the mixture is stirred at 0° C. for 3 hours. For working up, the mixture is stirred into 20 ml of saturated NaHCO$_3$ solution and the organic phase is separated off and dried over MgSO$_4$. After the solvent has been evaporated off in vacuo and the residue has been titrated with 5 ml of ether, 224 mg (43%) of the title compound are obtained as colourless crystals.

Melting point: 228° C.
R$_f$=0.16 (methylene chloride:methanol 95:5)
MS (FAB): m/z=354 (M+H)$^+$
$^1$H-NMR (250 MHz, D$_6$-DMSO): δ=1.85 (s, 3H, COCH$_3$); 3.10 (s, 3H, CH$_3$SO); 3.47 (t, J=6 Hz, 2H, CH$_2$N); 3.87 (dd, J=7, 10 Hz, 1H, H-4 trans); 4.23 (dd, J=10, 10 Hz, 1H, H-4 cis); 4.80 (m, 1H, H-5); 7.94 (m, 1H, benzothiazole H-5); 8.12 (d, J=10 Hz, 1H, benzothiazole H-4); 8.27 (m, 1H, NH); 8.38 (d, J=1.5 Hz, 1H, benzothiazole H-7).

Example 33

(5S)-3-(2-Benzylsulphonyl-benzo[4,5-d]thiazol-6-yl)-5-acetylaminomethyloxazolidin-2-one

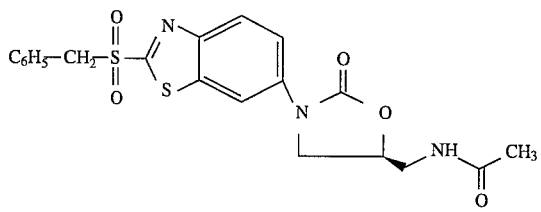

3.17 g (14.7 mmol) of 80% strength m-chloroperbenzoic acid are added to a stirred suspension of 2.50 g (6.13 mmol) of the compound from Example 27 in 25 ml of methylene chloride and the mixture is stirred at room temperature for 20 hours. Thereafter, the mixture is stirred into 50 ml of 10% strength Na$_2$SO$_3$ solution. The organic phase is separated off, washed with 50 ml of saturated NaHSO$_3$ solution and dried over MgSO$_4$. After the solvent has been evaporated off in vacuo and the residue has been chromatographed on 120 g of silica gel (ethyl acetate:acetone 9:1), 1.86 g (68%) of the title compound are obtained as colourless crystals.

Melting point: 194° C.
R$_f$=0.14 (ethyl acetate:acetone 9:1 )
MS (FAB): m/z=446 (M+H)$^+$
$^1$H-NMR (200 MHz, D$_6$-DMSO): δ=1.84 (s, 3H, COCH$_3$); 3.45 (t, J=6 Hz, 2H, CH$_2$N); 3.85 (dd, J=7, 10 Hz, 1H, H-4 trans); 4.22 (dd, J=9, 10 Hz, 1H, H-4 cis); 4.45, 4.70 (AB, J$_{AB}$=13 Hz 2H, CH$_2$SO$_2$); 4.80 (m, 1H, H-5); 7.10–7.35 (m, 5H, Ph); 7.93 (dd, J=1, 10 Hz 1H, benzothiazole H-5); 8.13 (d, J=10 Hz, 1H, benzothiazole H-4); 8.30 (m, 2H, NH, benzothiazole H-7).

Example 34

(5S)-3-(2-Cyclopropylamino-benzo[4,5-d]thiazol-6-yl)-5-acetylaminomethyloxazolidin-2-one

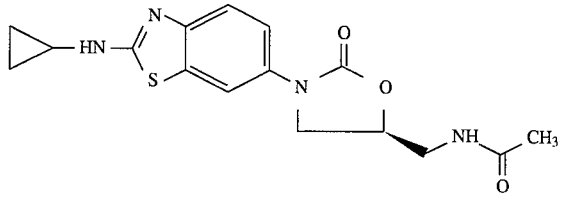

A suspension of 110 mg (0.30 mmol) of the compound from Example 37 and 730 μl (10.5 mmol) of cyclopropylamine in 1 ml of anhydrous acetonitrile is heated under reflux for 48 hours. The mixture is allowed to cool and the resulting precipitate is separated off, washed with 0.5 ml of acetonitrile and dried under a high vacuum. 60 mg (58%) of the title compound are obtained as colourless crystals.

Melting point: 226° C. (decomposition)
R$_f$=0.26 (methylene chloride:methanol 92:8)
MS (DCI, NH$_3$): m/z=347 (M+H)$^+$
$^1$H-NMR (200 MHz, D$_6$-DMSO): δ=0.58, 0.78 (m, 4H, cyclopropyl H); 1.82 (s, 3H, COCH$_3$); 2.70 (m, 1H, cyclopropyl H); 3.43 (t, J=6 Hz, 2H, CH$_2$N); 3.77 (dd, J=7, 10 Hz, 1H, H-4 trans); 4.12 (dd, J=10, 10 Hz, 1H, H-4 cis); 4.71 (m, 1H, H-5); 7.42 (s, 2H, benzothiazole H); 7.89 (s, 1H, benzothiazole H); 8.20-8.35 (m, 2H, NH).

Example 35

(5S)-3-[2-(Pyridin-2-yl)thio-benzo[4,5d]thiazol-6-yl]-5-acetylaminomethyloxazolidin-2-one

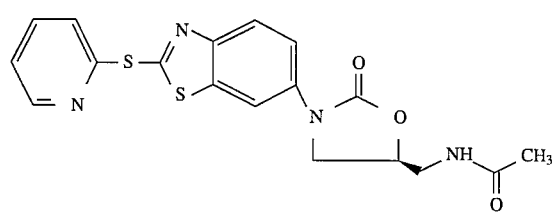

165 mg (1.48 mmol) of 2-mercaptopyridine are added to a stirred suspension of 300 mg (0.67 mmol) of the compound from Example 33 and 0.22 ml (1.55 mmol) of triethylamine in 3 ml of acetonitrile and the mixture is heated at 60° C. for 21 hours. The mixture is allowed to cool, the solvent is evaporated off in vacuo and the residue is purified over 45 g of silica gel (methylene chloride:methanol 95:5). 119 mg (44%) of the title compound are obtained as colourless crystals.

Melting point: 129° C.
R$_f$=0.06 (methylene chloride: methanol 95:5)
Ms (DCI, NH$_3$): M/z=401 (M+H)$^+$
$^1$H-NMR (200 MHz, D$_6$-DMSO): δ=1.83 (s, 3H, COCH$_3$); 3.45 (m, 2H, CH$_2$N); 3.72 (dd, J=7, 10 Hz, H-4 trans); 4.20 (dd, J=10, 10 Hz, 1H, H-4 cis); 4.78 (m, 1H, H-5); 7.5 (m, 1H, pyridyl H-5); 7.70 (d, J=10 Hz 1H, benzothiazole H-4); 7.8–8.0 (m, 4H); 8.20 (d, J=1 Hz, 1H, benzothiazole H-7); 8.28 (t, J=6 Hz, 1H, NH); 8.62 (m, 1H, pyridyl H-6).

As described for Examples 32, 33 and 35, the following compounds are obtained (Table 5):

is then flushed with nitrogen for 10 minutes in order to remove excess ozone, and 1.90 mg (26.50 mmol) of dim-

TABLE 5

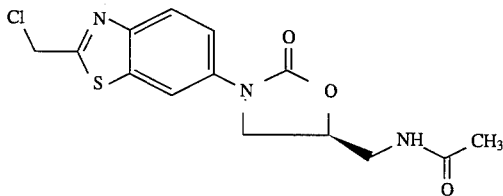

| Ex. No. | $R^{23}$ | c | Analogously to Example No. | Yield[%] of theory] | Melting point [°C.] | $R_f$/ mobile phase (ratio) | $[\alpha]_D^{20}$ (DMSO) | MS (FAB) m/z (M + H)⁺ |
|---|---|---|---|---|---|---|---|---|
| 36 | $C_6H_5-H_2C-$ | 1 | 32 | 50 | 188 | 0.35, I (9:1) | | 430 |
| 37 | $H_3C-$ | 2 | 33 | 40 | 197 | 0.14, I (95:5) | | 370 |
| 38 | 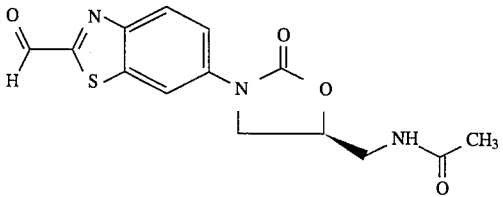 | 0 | 35 | 9 | 192 (decomp.) | 0.17, I (95:5) | | 402 |

Example 39

(5S)-3-(2-Chloromethyl-benzo[4,5-d]thiazol-6-yl)-5-acetamidomethyl-oxazolidin-2-one A suspension of 153 mg (0.50 mmol) of the compound from Example 26 in 3 ml of sulphuryl chloride is heated at 90° C. in the presence of 10 mg of azoisobutyronitrile for 11 hours. During the reaction, 3 portions of 10 mg of azoisobutyronitrile are subsequently added. For working up, the mixture is poured into 50 ml of ether and the precipitate is separated off by filtration, washed with 3 portions of 5 ml of ether and dried under a high vacuum. 120 mg (71%) of the title compound are obtained as an amorphous solid.
$R_f$=0.16 (methylene chloride:methanol 95:5)
MS (FAB): m/z=340 (M+H)⁺

Example 40

(5S)-3-(2-Formyl-benzo[4,5-d]thiazol-6-yl)-5-acetaminomethyl-oxazolidin-2-one

An ozone/oxygen mixture is passed through a solution, cooled to −78° C., of 2.50 g (6.35 mmol) of the compound from Example 28 in 125 ml of methylene chloride and 12 ml of methanol until a blue coloration is obtained. The mixture ethyl sulphide are subsequently added. The mixture is stirred at −10° C. for 30 minutes and at room temperature for 1 hour, tested for the absence of ozonide and then concentrated in vacuo. The residue is taken up in 50 ml of methylene chloride and the mixture is washed with saturated NaHCO₃ solution and dried over MgSO₄. After the solvent has been evaporated off and the residue has been titrated with 25 ml of ether, 1.70 g (79%) of the title compound are obtained as crystals.

Example 41

(5S)-3-[5-(2-Hydroxymethyl-benzo[4,5-d]thiazol-6-yl)-5-acetyl-aminomethyl-oxazolidin-2-one

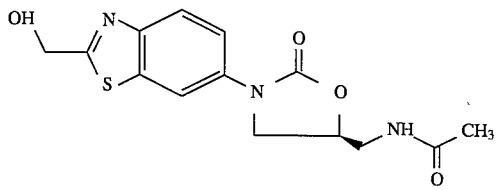

10 mg (0.26 mmol) of sodium borohydride are added to a stirred solution, cooled to 0° C., of 82 mg (0.26 mmol) of the compound from Example 40 in 3 ml of methanol and the mixture is stirred at 0° C. for 4 hours. The solvent is evaporated off in vacuo and the residue is purified by chromatography over 2 g of silica gel (methylene chloride:methanol). 51 mg (61%) of the title compound are obtained as colourless crystals.
Melting point: 180°–182° C.
$R_f$=0.20 (methylene chloride:methanol 9:1 )
MS (DCI, NH₃): m/z=322 (M+H)⁺, 339 (M+NH₄)⁺
¹H-NMR (250 MHz, D₆-DMSO): δ=1.86 (s, 3H, COCH₃); 3.45 (m, 2H, CH₂N); 3.83 (dd, J=8.10 Hz, 1H, H-4 trans); 4.20 (dd, J=10, 10 Hz, 1H, H-4-cis); 4.76 (m, 1H, H-5); 4.85 (d, J=5 Hz, 2H, CH₂OH); 7.76 (dd, J=1.10 Hz, 1H, benzothiazole H-5); 7.92 (d, J=10 Hz 1H, benzothiazole H-4); 8.20 (d, J=1 Hz, 1H, benzothiazole H-7); 8.25 (m, 1H, NHCO).

Example 42

(5S)-3-(2-Methylthio-3-methyl-benzo[4,5-d]thiazol-6-yl)-5-(acetylaminomethyl)-oxazolidin-2-one iodide

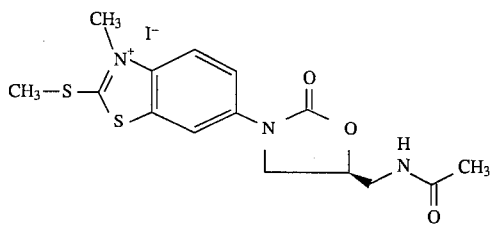

2.6 ml (40.00 mmol) of iodomethane are added to a stirred solution of 1.35 g (4.00 mmol) of the compound from Example 24 in 6 ml of anhydrous DMF and the mixture is heated at 70° C. for 23 hours.

Thereafter, the reaction mixture is allowed to cool, 80 ml of ether are added and the resulting precipitate is separated off by filtration. After stirring in 50 ml of ethanol, renewed filtration and drying of the product under a high vacuum over Sicapent, 1.17 g (61%) of the title compound are obtained as colourless crystals.

Melting point: 149° C. (decomposition)

The title compound can also be obtained as described above in a yield of 79% from the compound from Example 27.

MS (FAB) m/z=352 (cation M⁺)

$^1$H-NMR (250 MHz, DMSO-$d_6$) δ=8.60 (d, J=1 Hz, 1H, benzothiazole (H-7); 8.28 (m, 1H, NHCO); 8.20 (d, J=10 Hz 1H, benzothiazole H-4); 8.02 (dd, J=1, 10 Hz, 1H, benzothiazole H-5); 4.82 (m, 1H, H-5); 4.20 (dd, J=10, 10 Hz, 1H, H-4 cis); 4.10 (s, 3H, NCH$_3$); 3.85 (dd, J=7, 10 Hz, 1H, H4 trans); 3.46 (m, 2H, CH$_2$N); 3.12 (s, 3H, SCH$_3$); 1.85 (2, 3H, COCH$_3$).

Example 43

(5R)-3-(2-[4'-Chloro-styryl]-benzo[4,5-d]thiazol-6-yl)-5-methanesulphonyloxy-methyloxazolidin-2-one

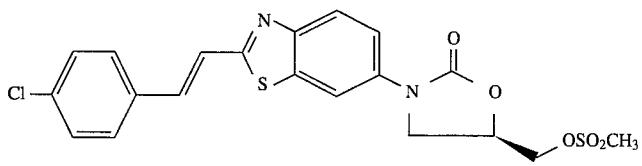

17.4 ml (125 mmol) of triethylamine are added to a suspension of 24.2 g (63 mmol) of the compound from Example XXII in 500 ml of absolute THF under argon and the mixture is cooled to 0° C.

6.1 ml (78 mmol) of methanesulphonyl chloride are slowly added and the mixture is subsequently stirred at 0° C. for 1 hour.

The mixture is allowed to come to room temperature overnight and is poured onto 4 l of ice-water. H is subsequently stirred briefly and the product which has precipitated out is then filtered off with suction. H is rinsed with water until the wash water gives a neutral reaction. The product is dried under a high vacuum. 28 g (96%) of the title compound are obtained as yellow crystals.

Melting point: 231° C.

$R_f$=0.23 (toluene:ethyl acetate =1:2)

MS (FAB) m/z=465 (M+H)⁺

$^1$H-NMR (200 MHz, DMSO-$d_6$): δ=8.25 (d, J=1.5, 1H, benzothiazole H-7); 8.00 (d, J=9.5, 1H, benzothiazole H-4); 7.80 (m, 3H, benzothiazole H-5, phenyl H-3.5); 7.64 (s, 2H, vinyl); 7.50 (d, J=9, 2H, phenyl H-2.6); 5.06 (m, 1H, H-5); 4.53 (m, 2H, CH$_2$OMs); 4.30 (dd, J=9.5, 1H, H-4); 3.94 (dd, J=9.5, J=6, 1H, H4); 3.33 (s, 3H, OSO$_2$CH$_3$).

The compounds listed in Table 6 are prepared analogously to the instructions of Example 9

TABLE 6

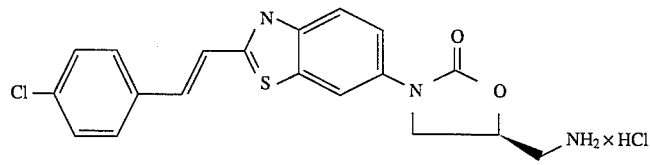

| Ex No. | D | Yield (% of theory) | Melting point (°C.) | $R_f$ | MS |
|---|---|---|---|---|---|
| 44 | Cl-C6H4-CH=CH-benzothiazole-CH3 | 92 | 209 with decomposition | 0.80 I (195:5) | 412[a] |

[a] = MS (DCI, NH$_3$) m/z = (M + H)$^+$

Example 45

(5S)-3-(2-[4'-Chloro-styryl]-benzo[4,5-d]thiazol-6-yl)-5-aminomethyl-oxazolidin-2-one hydrochloride

Example 46

(5S)-3-(2-[4'-Chloro-styryl]-benzo[4,5-d]thiazol-6-yl)-5-acetaminomethyl-oxazolidin-2-one 11.5 ml (67 mmol) of triethyl phosphite are slowly added dropwise to a suspension, stirred at 50° C., of 23 g (56 mmol) of the compound from Example 44 in 200 ml of dimethoxyethane (evolution of gas!).

When the evolution of gas has ended, the mixture is heated at 90° C. for 1 hour. 23 ml of 6N HCl are added and the mixture is subsequently stirred at 90° C. for 36 hours. H is cooled to room temperature, 200 ml of diethyl ether are added, the mixture is subsequently stirred for 15 minutes and the precipitate is filtered off with suction. It is washed with

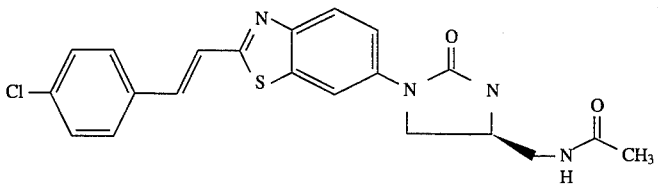

diethyl ether and dried first in a high vacuum and then in a circulating air drying cabinet at 70° C.

23.0 g (98%) of the title compound are obtained as a yellow solid.

Melting point: >255° C.

$R_f$=0.12 (CH$_2$Cl$_2$:MeOH:NH$_{3(aq)}$=100:5:2)

$^1$H-NMR (200 MHz, DMSO-d$_6$): δ8.57 (s, broad, 3H, N$^{61}$H$_3$); 8.24 (d, J=1.5, 1H, H-7); 8.01 (d, J=9.5, 1H, H-4); 7.80 (m, 3H, benzothiazole H-5, phenyl H-3.5); 7.65 (s, 2H, vinyl); 7.50 (d, J=9, 2H, phenyl H-2.6); 5.05 (m, 1H, H-5); 4.30 (dd, J =9.5, J=9.5, 1H, H-4); 4.02 (dd, J=9.5, J=6, 1H, H-4); 3.29 (m, 2H, CH$_2$ -NH$_2$)

MS (EI) m/z=385 (M$^+$)

23.7 ml (136 mmol) of diisopropylethylamine are added to a suspension, stirred under argon, of 23 g (55 mmol) of the compound from Example 45 in 500 ml of THF (absolute) and the mixture is cooled to 0° C. 5.8 ml (80 mmol) of acetyl chloride are added and the mixture is subsequently stirred at 0° C. for 30 minutes.

The mixture is allowed to come to room temperature and is poured onto 4.5 l of water.

After stirring for 15 minutes, the precipitate is filtered off with suction and washed with water. The solid is extracted by stirring again with water and is filtered off with suction again. The product is then dried in a circulating air drying cabinet at 80° C. 21.1 g (90%) of the title compound are obtained as beige crystals.

Melting point: 253° C. with decomposition $R_f$=0.22 (CH$_2$Cl$_2$: MeOH:NH$_{3(aq)}$=100:5:2)

MS (EI): m/z=427 (M)$^+$

[α]$_D^{20}$=(DMSO)=−29.3° (C=1)

$^1$H-NMR (300 MHz, DMSO-d$_6$): δ=8.28 (tr, J=5.5, 1H, NH); 8.20 (d, J=1.5, 1H, H-7); 7.99 (d, J=9.5, 1H, H-4); 7.80 (m, 3H, benzothiazole H-5, phenyl H-3.5); 7.62 (s, 2H, vinyl); 7.50 (d, J=9, 2H, phenyl H-2.6); 4.78 (m, 1H, H-5); 4.22 (dd, J=9.5, J=9.5, 1H, H-4); 3.85 (dd, J=9.5, J=6.5, 1H, H-4); 3.46 (dd, J=5.5, J=5.5, 2H, CH$_2$-NH); 1.85 (s, 3H, COCH$_3$).

Example 47

(5S)-3-(2-[3'-Butenyl]-benzo[4,5-d]-5-yl)-5-acetaminomethyl-oxazolidin-2-one

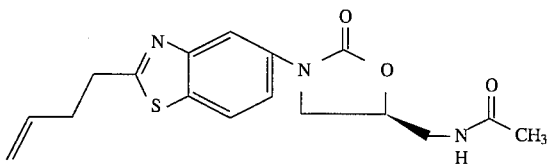

A solution of 20 mg (0.065 mmol) of the compound from Example 30 is dissolved in 1 ml of absolute THF under argon and the solution is cooled to −76° C. 0.235 ml of a freshly prepared 0.83 molar LDA solution (0.195 mmol) is added and the mixture is stirred at −76° C. for 1 hour. 5.6 µl (0.065 mmol) of allyl bromide are added and the mixture is stirred at −76° C. for 1 hour. H is allowed to warm to room temperature, 10 ml of H$_2$O are added, the mixture is extracted 3 times with ethyl acetate and the extract dried over MgSO$_4$ and concentrated. The residue is purified over silica gel using ethyl acetate:MeOH=100:4 to give 12.4 mg (55%) of the title compound.

$R_f$=0.20 (ethyl acetate:MeOH=100:4)

MS (EI): m/z=345 (M$^+$)

$^1$H-NMR (200 MHz, DMSO-d$_6$): δ=8.15 (tr, J=6, 1H, NH); 7.9 (m, 2H, benzothaizole H-4.7); 7.55 (dd, J=9.5, J=2, 1H, H-6); 5.77 (m, 1H—CH=CH$_2$); 4.98 (m, 1H, CH=CH$_2$); 4.89 (m, 1H, CH=CH$_2$); 4.62 (m, 1H, H-5); 4.09 (dd, J=9.5, J=9.5, 1H, H-4); 3.70 (dd, J=9.5, J=6, 1H, H-4); 3.30 (dd, J=6, J=6, 2H, CH$_2$-NH); 3.06 (tr, J=7.5, 2H, CH$_2$—CH$_2$—CH=CH$_2$); 2.45 (m, 2H, CH$_2$—CH=CH$_2$); 1.70 (s, 3H, COCH$_3$).

Example 48

(5S)-3-[2-(Ethoxycarbonylmethylthio)benzoxazol-6-yl]-5-acetylaminomethyl-oxazolidin-2-one

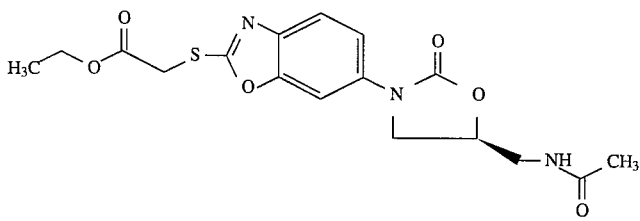

290 mg (1.1 mmol) of the compound from Example XXXVI and 193 mg (1.2 mmol) of potassium O-ethyldithiocarbonate in 6 ml of ethanol are stirred at 70° C. for 8 hours. The solvent is stripped off, the residue is suspended in 20 ml of methanol and 265 mg (1.6 mmol) of ethyl bromoacetate are added. After 1 hour at 0° C., 40 ml of water are added, the aqueous phase is extracted with ethyl acetate, the combined organic phases are dried (Na$_2$SO$_4$) and the solvents are stripped off. The residue is recrystallized from methanol.

Yield: 155 mg (36%)

$R_f$=0.67 (VII, 1:1)

Melting point: 146°–147° C.

[α]$_D^{20}$=−19.05 (c=0.5, DMSO)

MS (FAB): m/z=394 (M$^+$+H)

$^1$H-NMR (250 MHz, D$_6$-DMSO): 1.20 (t, 3H, CH$_3$); 1.80 (s, 3H, NHCOCH$_3$); 3.35–3.45 (m, 2H, CH$_2$N), 3.80 (dd, 1H, H-4 ), 4.10–4.25 (m, 3H, CO$_2$CH$_2$, H-4), 4.70–4.85 (m, 1H, H-5), 7.48 (dd, 1H; benzoxazole H-5), 7.60 (d, 1H, benzoxazole H-4), 7.90 (d, 1H, benzoxazole H-7), 8.23 (bs, 1H, NH).

The compounds listed in Table 7 are prepared analogously to the instructions of Example 48.

TABLE 7

[Structure: D—N linked to oxazolidinone ring with CH₂—NH—C(=O)CH₃ substituent]

| Ex. No. | D | Yield [% of theory] | Melting point [°C.] | R_f Mobile phase (ratio) | $[\alpha]_D^{20}$ (DMSO) | MS (FAB) m/z (M + H)⁺ |
|---|---|---|---|---|---|---|
| 49 | CH₃—S— (benzoxazole, 5-linked) | 92 | 205–206 | 0.65 VII (1:1) | −21.9 (c = 1.0) | 321[a] |
| 50 | CH₃—S— (benzoxazole, 6-linked) | 83 | 163–165 | 0.62 VII (1:1) | — | 321[a] |
| 51 | Allyl-S— (benzoxazole, 5-linked) | 40 | 181–182 | 0.59 VII (1:1) | −19.0 (c = 1.0) | 347[a] |
| 52 | Allyl-S— (benzoxazole, 6-linked) | 47 | 145–147 | 0.60 VII (1:1) | −19.0 (c = 1.0) | 347[a] |
| 53 | C₆H₅—S— (benzoxazole, 5-linked) | 60 | 169–170 | 0.65 VII (1:1) | −15.9 (c = 0.5) | 397[a] |
| 54 | C₆H₅—S— (benzoxazole, 6-linked) | 30 | 150–151 | 0.77 VII (1:1) | — | 397[a] |
| 55 | C₁₂H₂₅—S— (benzoxazole, 5-linked) | 56 | 158–159 | 0.73 VII (1:1) | −15.1 (c = 0.5) | 476 |
| 56 | C₁₂H₂₅—S— (benzoxazole, 6-linked) | 30 | 147–148 | 0.65 VII (1:1) | — | 476 |

[a] MS (EI) m/z = (M)⁺

Example 57

(5S)-3-(Benzoxazol-6-yl)-5-acetylaminomethyloxazolidin-2-one

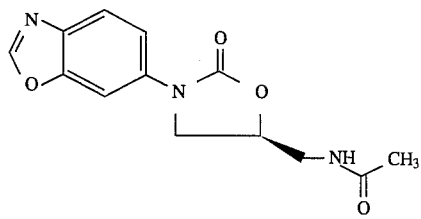

A mixture of 500 mg (1.88 mmol) of the compound from Example XXXVI, 50 μl of concentrated hydrochloric acid and 13 ml of triethyl orthoformate is stirred at room temperature for 2 days. The excess orthoester is stripped off in vacuo and the residue is purified by chromatography.

Yield: 363 mg (70%)
R_f: 0.18 (VII, 5:1)
Melting point: 186.5° C.
$[\alpha]_D^{20}$=26.7 (c=1.0, DMSO)
MS (EI): m/z, 272
¹H-NMR (250 MHz, D₆-DMSO): δ=1.85 (s, 3H, COCH₃); 3.47 (t, J=6 Hz, 2H, CH₂N); 3.87 (dd, J=7, 10 Hz, 1H, H-4); 4.23 (dd, J=10, 10 Hz, 1H, H-4); 4.80 (m, 1H, H-5); 7.55 (dd, 1H, benzoxazole H-5); 7.80 (d, J=10 Hz, 1H, benzoxazole H-4); 7.95 (d, J=1.5 Hz, 1H, benzoxazole H-7); 8.25 (bt, J=1.5 Hz, NH); 8.70 (s, 1H, benzoxazole H-2).

The compounds listed in Table 8 are prepared analogously to the instructions of Example 57.

TABLE 8
| Ex. No. | | Yield (% of theory) | $R_f$ | Melting point: (°C.) | $\alpha_D$ | Ms (EI) m/z (M⁺) |
|---|---|---|---|---|---|---|
| 58 |  | 50 | 0.47 VII (1:1) | 170 | −26.7 (c = 1.0) | 275 |
The compounds listed in Table 9 are prepared by the following methods:
TABLE 9
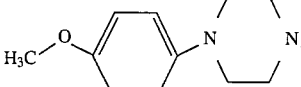
| Ex. No. | R² | Method | Yield (% of theory) | Melting point °C. | $R_f$ value mobile phase | MS m/z (M + H)⁺ |
|---|---|---|---|---|---|---|
| 59 | 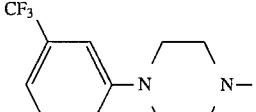 | 1) | 85 | >250 | 0.5 (I) 10:1 | 482 |
| 60 | 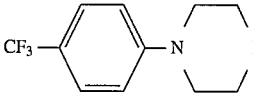 | 1) | 26.4 | 225 | 0.35 (I) 10:1 | 520 |
| 61 | 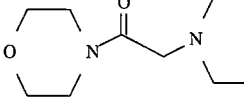 | 1) | 85 | >250 | 0.35 (I) 10:1 | 520 |
| 62 | 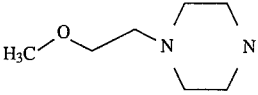 a) | 1) | 61.8 | 219 | 0.39 (I) 10:1 | 503 |
| 63 | 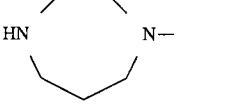 | 2) | 55.2 | 147 | 0.35 (I) 10:1 | 434 M⁺ᴺ |
| 64 | 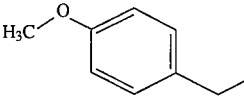 | 2) | 96 | amorphous | 0.12 (I) 10:1 | 390 |
| 65 | 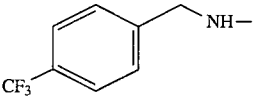 | 1 | 95.8 | 168 | 0.45 (I) 10:1 | 441 |
| 66 |  | 1) | 35.6 | 203 | 0.54 (I) 10:1 | 465 |

TABLE 9-continued

[Structure: R²-substituted benzothiazole with -N-C(=O)-O-CH₂-*CH-CH₂-NH-CO-CH₃]

| Ex. No. | R² | Method | Yield (% of theory) | Melting point °C. | R_f value mobile phase | MS m/z (M + H)⁺ |
|---|---|---|---|---|---|---|
| 67 | piperidine-3-carboxamide, N-methyl | 1) | 85.9 | 214 | 0.39 (I) 10:1 | 418 |
| 68 | 4-(dimethylamino)pyridinium | 1) | 48.1 | 221 decomp. | — | 412 7) |
| 69 | 2-methoxypyridin-yl | 1) | 90 | >250 | 0.53 (I) 10:1 | 385 |
| 70 | HO-CH₂CH₂-NH- | 1) | 47 | 183 | 0.14, I (9:1) | 351 |
| 71 | HO-CH₂CH₂CH₂-NH- | 1) | 42 | 182 | 0.20, I (9:1) | 365 |
| 72 | HO-CH₂CH₂-O-CH₂CH₂-NH- | 1) | 53 | 73 | 0.40, I (9:1) | 395 |
| 73 | HO-CH₂CH₂-N(imidazolyl) | 1) | 68 | 149 | 0.37, III (4:1) | 406 |
| 74 | CH₃-CH(OH)-CH₂-NH- | 1) | 59 | 93 | 0.19, I (9:1) | 365 |
| 75 | HO-CH₂-C(CH₃)₂-NH- | 1) | 43 | — | 0.12, I (9:1) | 379 |
| 76 | 2-pyridyl-piperazinyl | 1) | 85.7 | 223–224 | 0.46 | 453 |
| 77 | piperonyl-piperazinyl | 1) | 28 | 206–207 | 0.4 | 510 |
| 78 | morpholino-ethyl-piperazinyl | 1) | 83.8 | 181–182 | 0.11 | 489 |

TABLE 9-continued

| Ex. No. | R² | Method | Yield (% of theory) | Melting point °C. | R_f value mobile phase | MS m/z (M + H)⁺ |
|---|---|---|---|---|---|---|
| 79 | pyrazinylmethyl-piperazinyl | 1) | 80.7 | >250 | 0.36 | 454 |
| 80 | 4-nitrophenyl-piperazinyl | 1) | 30.5 | >250 | 0.44 | 497 |
| 81 | cyclopropylmethoxy | 3) | 30 | 165–167 | 0.46 | 362 |
| 82 | (dimethylamino)ethyl-piperazinyl | 1) | 42 | 183 | 0.2/I (10:1) | 447 |
| 83 | 1,4-dioxa-8-azaspiro[4.5]decan-8-yl | 1) | 47 | 188 | 0.45/I (10:1) | 432 |
| 84 | 4-hydroxypiperidin-1-yl | 1) | 65 | 211 | 0.2/I (10:1) | 391 |
| 85 | 3-(piperidin-1-yl)propylamino | 1) | 19 | 131 | 0.05/I (10:1) | 432 |
| 86 | 1,3-benzodioxol-5-ylmethylamino | 1) | 31 | 227 | 0.35/I (10:1) | 441 |
| 87 | pyridin-2-ylmethylamino | 1) | 52 | 214 | 0.2/I (10:1) | 398 |
| 88 | 3-(dimethylamino)propyl-methylamino | 1) | 43 | 114 | 0.2/I (10:1) | 406 |
| 89 | 4-(tert-butoxycarbonyl)piperazin-1-yl | 1) | 38 | 208 | 0.45/I (10:1) | 476 |
| 90 | piperazin-1-yl × HCl | 4) | 99 | 201 | — | 376 |

TABLE 9-continued

[Structure: benzothiazole with R² substituent at position 2, and at position 6 an NH-C(=O)-O-CH₂-CH(*)-NH-CO-CH₃ group]

| Ex. No. | R² | Method | Yield (% of theory) | Melting point °C. | R_f value mobile phase | MS m/z (M + H)⁺ |
|---|---|---|---|---|---|---|
| 91 | [piperidone-N—, O=C< ring with N—] | 5) | 90 | — | 0.49/I (10:1) | 389 |
| 92 | [2-pyridyl-CH₂-NH— ×HCl] | 6) | 99 | — | — | — |
| 93 | [CH₃-CH(NH—)-C(=O)-N(CH₃)H] | 1) | 43 | 207 with decomp. | — | — |

1) Heat 1 mmol of sulphone 37 with 10 mmol of the nucleophile in 4 ml of acetonitrile under reflux for 2 days. Working up as for Example 34 or 35.
2) Heat 1 mmol of sulphone 37 with 35 mmol of nucleophile in 4 ml of acetonitrile under reflux for 2 days. Working up as in Example 34 or 35.
3) 1.05 mmol of the nucleophile in 4 ml of DMF are added to 1.05 mmol of KH, and 1 mmol of sulphone 37 is then added at 0° C. The mixture is allowed to come to room temperature and is stirred for 1 hour. Diethyl ether is added and the product is filtered off with suction.
4) Reaction of Example 89 with 6N HCl/dioxane
5) Reaction of Example 83 with 4N HCl/dioxane
6) Reaction of Example 87 with HCl/ether
7) M⁺ of the cation, counter-ion $CH_3SO_2^-$

We claim:

1. Compounds of the general formula (I)

[Formula (I): benzothiazole-type bicyclic core with positions labeled G(4), L(5), M(6), 7, A; R² attached to the 2-position; at position 5/6 an N-C(=O)-O-CH₂-CH(*)-R¹ group]

in which

A represents an oxygen atom, or represents a radical of the formula —S(O)_a, wherein
a denotes the number 0 or 2, R¹ represents azido, or represents a group of the formula O—SO₂R³ or —NR⁴R⁵, wherein R³ denotes straight-chain or branched alkyl having up to 4 carbon atoms, or phenyl which is optionally substituted by straight-chain or branched alkyl having up to 4 carbon atoms, R⁴ and R⁵ are identical or different and denote cycloalkyl having 3 to 6 carbon atoms, hydrogen, phenyl or straight-chain or branched alkyl having up to 8 carbon atoms or an amino-protective group, or R⁴ or R⁵ denote a group of the formula —CO—R⁶, wherein R⁶ denotes cycloalkyl having 3 to 6 carbon atoms, straight-chain or branched alkyl or alkoxy having in each case up to 8 carbon atoms, phenyl or hydrogen, G, L and M are identical or different and represent hydrogen, carboxyl, halogen, cyano, formyl, trifluoromethyl, nitro or straight-chain or branched alkoxy, alkoxycarbonyl, alkylthio or acyl having in each case up to 6 carbon atoms, or represent straight-chain or branched alkyl having up to 6 carbon atoms, which can in turn be substituted by hydroxyl, by straight-chain or branched alkoxy or acyl having up to 5 carbon atoms or by a group of the formula —NR⁷R⁸, wherein R⁷ and R⁸ are identical or different and denote hydrogen, straight-chain or branched alkyl having up to 4 carbon atoms or phenyl, or together with the nitrogen atom form a 5- to 6-membered saturated heterocyclic ring with optionally a further hetero atom from the series consisting of N, S and/or O, which can in turn optionally be substituted, also on another nitrogen atom, by straight-chain or branched alkyl or acyl having up to 3 carbon atoms, and/or optionally represent a group of the formula —NR⁷'R⁸', wherein R⁷' and R⁸' are identical or different and have the above-mentioned meaning of R⁷ and R⁸ and are identical to or different from these, and/or optionally represent (C₂-C₈)-alkenylphenyl, phenyl or a 5- or 6-membered saturated or unsaturated heterocyclic radical having up to 3 hetero atoms from the series consisting of S, N and/or O, each of which is in turn optionally substituted by a group of the formula —CO—NR⁹R¹⁰, NR¹¹R¹², NR¹³—SO₂—R¹⁴, R¹⁵R¹⁶N—SO₂— or R¹⁷—S(O)_b—, wherein b denotes the number 0, 1 or 2, $R^9$, $R^{10}$, $R^{13}$, $R^{15}$ and $R^{16}$ are identical or different and denote hydrogen, straight-chain or branched alkyl having up to 6 carbon atoms or phenyl, $R^{11}$ and $R^{12}$ are identical or different and have the abovementioned meaning of $R^7$ and $R^8$ and are identical to or different from these, $R^{14}$ and $R^{17}$ are identical or different and have the abovementioned meaning of $R^3$ and are identical to or different from this, and/or are in turn optionally substituted up to twice in an identical or different manner by carboxyl, halogen, cyano, formyl, trifluoromethyl, nitro, phenyl, straight-chain or branched alkoxy, alkoxycarbonyl, alkylthio or acyl having in each case up to 6 carbon atoms or by straight-chain or branched alkyl having up to 6 carbon atoms, which can in turn by substituted by hydroxyl, by straight-chain or branched alkoxy or acyl having up to 5 carbon atoms or by a group of the formula —$NR^{18}R^{19}$, wherein $R^{18}$ and $R^{19}$ have the abovementioned meaning of $R^7$ and $R^8$ and are identical to or different from these, $R^2$ represents hydrogen, formyl or carboxyl, or represents straight-chain or branched alkoxycarbonyl having up to 6 carbon atoms, or represents straight-chain or branched alkyl or alkenyl having in each case up to 8 carbon atoms, each of which is optionally substituted by hydroxyl, halogen or by straight-chain or branched alkoxy, acyl, alkylthio or alkoxycarbonyl having in each case up to 6 carbon atoms or phenyl, which can in rum be substituted by halogen, or represents aryl having 6 to 10 carbon atoms, which is optionally substituted by carboxyl, halogen, cyano, formyl, trifluoromethyl, nitro, straight-chain or branched alkoxy, alkoxycarbonyl, alkylthio or acyl having in each case up to 6 carbon atoms or by straight-chain or branched alkyl having up to 6 carbon atoms, or represents a radical of the formula —$NR^{20}$ $R^{21}$, —$OR^{22}$ or —$S(O)_c$—$R^{23}$, wherein $R^{20}$ denotes cycloalkyl having 3 to 6 carbon atoms, phenyl, straight-chain or branched acyl having up to 6 carbon atoms or straight-chain or branched alkyl having up to 8 carbon atoms, which is optionally substituted by hydroxyl, straight-chain or branched alkoxy or hydroxy-substituted alkoxy having in each case up to 6 carbon atoms, by a 5- to 6-membered aromatic heterocyclic radical having up to 3 hetero atoms from the series consisting of S, N and/or O, or by phenyl, which can in turn be substituted by hydroxyl, trifluoromethyl, halogen, nitro or by straight-chain or branched alkoxy having up to 4 carbon atoms, or alkyl is optionally substituted by a radical of the formula —$NR^{24}R^{25}$ or

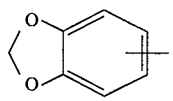

wherein $R^{24}$ and $R^{25}$ are identical or different and denote hydrogen or straight-chain or branched alkyl having up to 4 carbon atoms, or $R^{20}$ denotes a radical of the formula

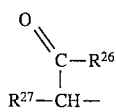

wherein $R^{26}$ denotes hydroxyl, straight-chain or branched alkoxy having up to 4 carbon atoms or a radical of the formula —$NR^{28}R^{29}$, wherein, $R^{28}$ and $R^{29}$ are identical or different and denote hydrogen or straight-chain or branched alkyl having up to 5 carbon atoms, cycloalkyl having 3 to 6 carbon atoms or phenyl, R,$^{27}$ denotes hydrogen or straight-chain or branched alkyl having up to 7 carbon atoms, which is optionally substituted by indolyl, hydroxyl, mercaptyl, imidazolyl, methylthio, amino, phenyl, hydroxy-substituted phenyl or by a radical of the formula —CO—$NH_2$, —$CO_2H$ or

or $R^{20}$ denotes a radical of the formula

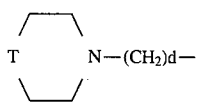

wherein d denotes the number 0, 1, 2, 3, 4, 5 or 6,

T denotes an oxygen atom or a group of the formula $CH_2$ or —$NR^{30}$, wherein $R^{30}$ denotes hydrogen, phenyl or straight-chain or branched alkyl having up to 6 carbon atoms, which is optionally substituted by hydroxyl, and $R^{21}$ has the abovementioned meaning of $R^{20}$ and is identical to or different from this, or denotes hydrogen, $R^{22}$ denotes straight-chain or branched alkyl having up to 8 carbon atoms, which is optionally substituted by straight-chain or branched alkoxy or hydroxy- or alkoxy-substituted alkoxy having in each case up to 6 carbon atoms, cycloalkyl having 3 to 6 carbon atoms or a 6-membered aromatic, optionally benzo-fused heterocyclic radical having up to 3 nitrogen atoms, which can in turn be substituted up to twice in an identical or different manner by nitro, trifluoromethyl, halogen, cyano, hydroxyl or by straight-chain or branched alkyl, alkoxy or acyl having in each case up to 5 carbon atoms, or $R^{22}$ denotes a radical of the formula

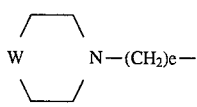

wherein e has the abovementioned meaning of d and is identical to or different from this, different from this, W has the abovementioned meaning of T and is identical to or different from this, or $R^{22}$ denotes phenyl or pyridyl, c denotes a number 0, 1 or 2, $R^{23}$ denotes straight-chain or branched alkyl or alkenyl having up to 16 carbon atoms, which is optionally substituted by straight-chain or branched alkoxycarbonyl having up to 6 carbon atoms or phenyl or by a 5- to 7-membered aromatic heterocyclic radical having up to 3 hetero atoms from the series consisting of S, N and O, or denotes aryl having 6 to 10 carbon atoms or a 5- to 7-membered aromatic heterocyclic radical having up to 3 hetero atoms from the series consisting of S, N and O, and wherein the abovementioned cyclic radicals are optionally substituted up to twice in an identical or different manner by carboxyl, halogen, cyano, formyl, trifluoromethyl, nitro, straight-chain or branched alkoxy, alkoxycarbonyl, alkylthio or acyl having in each case up to 6 carbon atoms or by straight-chain or branched alkyl having up to 6 carbon atoms, or $R^2$ represents morpholinyl, or represents a radical of the formula

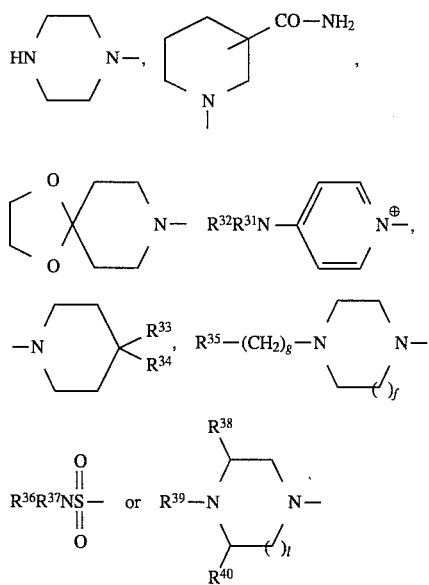

wherein $R^{31}$ and $R^{32}$ have the abovementioned meaning of $R^{24}$ and $R^{25}$ and are identical to or different from these, $R^{33}$ and $R^{34}$ together form a radical of the formula =O or $R^{33}$ and $R^{34}$ are identical or different and denote hydrogen, hydroxyl or straight-chain or branched alkyl having up to 6 carbon atoms, which is optionally substituted by a group of the formula —$NR^{41}R^{42}$ wherein $R^{41}$ and $R^{42}$ have the abovementioned meaning of $R^{24}$ and $R^{25}$ and are identical to or different from these, f denotes the number 0 or 1, g denotes the number 0, 1, 2, 3, 4, 5 or 6, $R^{35}$ denotes aryl having 6 to 10 carbon atoms or a 5- to 6-membered aromatic, optionally also benzo-fused heterocyclic radical having up to 3 hetero atoms from the series consisting of S, N and/or O, it being possible for all the ting systems to be substituted up to 3 times in an identical or different manner by nitro, cyano, hydroxyl, phenyl, halogen, trifluoromethyl or by straight-chain or branched alkyl, alkoxy or acyl having in each case up to 5 carbon atoms, or $R^{35}$ denotes morpholinyl, hydroxyl, straight-chain or branched alkoxy having up to 6 carbon atoms or a radical of the formula

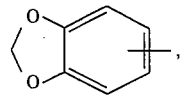

$NR^{43}R^{44}$ or —CO—$R^{45}$, wherein $R^{43}$ and $R^{44}$ are identical or different and have the abovementioned meaning of $R^{24}$ and $R^{25}$, $R^{45}$ denotes morpholinyl, hydroxyl or straight-chain or branched alkoxy having up to 6 carbon atoms, $R^{36}$ and $R^{37}$ are identical or different and denote hydrogen, phenyl or straight-chain or branched alkyl having up to 6 carbon atoms or benzyl, $R^{38}$, $R^{39}$ and $R^{40}$ are identical or different and have the abovementioned meaning of $R^{30}$ and are identical to or different from this, l denotes the number 1 or 2, and salts thereof.

2. Compounds according to claim 1, in which

A represents an oxygen atom, or represents a radical of the formula —$S(O)_a$, wherein a denotes the number 0 or 2, $R^1$ represents azido, or represents a group of the formula —$OSO_2R^3$ or —$NR^4R^5$, wherein $R^3$ denotes straight-chain or branched alkyl having up to 3 carbon atoms, phenyl or tolyl, $R^4$ and $R^5$ are identical or different and denote cyclopropyl, cyclopentyl, cyclohexyl, hydrogen, phenyl or straight-chain or branched alkyl or alkoxy having in each case up to 6 carbon atoms, tert-butoxycarbonyl or benzyloxycarbonyl, or $R^4$ or $R^5$ denotes a group of the formula —CO—$R^6$, wherein $R^6$ denotes cyclopropyl, cyclobutyl, cyclopentyl, cyclohexyl or straight-chain or branched alkyl or alkoxy having in each case up to 6 carbon atoms, phenyl or hydrogen, G, L and M are identical or different and represent hydrogen, carboxyl, fluorine, chlorine, bromine, iodine, cyano, trifluoromethyl, formyl, nitro or straight-chain or branched alkoxy, alkoxycarbonyl, alkylthio or acyl having in each case up to 3 carbon atoms, or represent straight-chain or branched alkyl having up to 4 carbon atoms, which can in turn be substituted by hydroxyl, by straight-chain or branched alkoxy or acyl having up to 4 carbon atoms or by a group of the formula —$NR^7R^8$, wherein $R^7$ and $R^8$ are identical or different and denote hydrogen, straight-chain or branched alkyl having up to 3 carbon atoms or phenyl, or together with the nitrogen atom form a morpholinyl, pyrrolidinyl, piperazinyl or piperidyl ring, each of which is optionally substituted, including via the free N function, by methyl, ethyl or acetyl, and/or optionally represent a group of the formula —$NR^{7'}R^{8'}$, wherein $R^{7'}$ and $R^{8'}$ have the abovementioned meaning of $R^7$ and $R^8$ and are identical to or different from these, and/or optionally represent (C$_2$–C$_4$)-alkenylphenyl, phenyl, pyridyl or thienyl, each of which is in turn optionally substituted by a group of the formula —CO—NR$^9$R$^{10}$, —NR$^{11}$R$^{12}$, —NR$^{13}$SO$_2$R$^{14}$, R$^{15}$R$^{16}$N—SO$_2$— or —R$^{17}$-S(O)$_b$— wherein b denotes the number 0, 1 or 2, R$^9$, R$^{10}$, R,$^{13}$, R$^{15}$ and R$^{16}$ are identical or different and denote hydrogen, straight-chain or branched alkyl having up to 4 carbon atoms or phenyl, R$^{11}$ and R$^{12}$ are identical or different and have the abovementioned meaning of R$^7$ and R$^8$ and are identical to or different from these, R$^{14}$ and R$^{17}$ are identical or different and have the abovementioned meaning of R$^3$ and are identical to or different from this, and/or are in turn optionally substituted up to twice in an identical or different manner by carboxyl, fluorine, chlorine, bromine, iodine, cyano, trifluoromethyl, formyl, nitro, phenyl, or straight-chain or branched alkoxy, alkoxycarbonyl, alkylthio or acyl having in each case up to 4 carbon atoms, or by straight-chain or branched alkyl having up to 4 carbon atoms, which can in turn optionally be substituted by hydroxyl, by straight-chain or branched alkoxy or acyl having up to 4 carbon atoms or by a group of the formula —NR$^{18}$R$^{19}$, wherein R$^{18}$ and R$^{19}$ have the abovementioned meaning of R$^7$ and R$^8$ and are identical to or different from these, R$^2$ represents hydrogen, formyl or carboxyl, or represents straight-chain or branched alkoxycarbonyl having up to 5 carbon atoms, or represents straight-chain or branched alkyl or alkenyl having in each case up to 6 carbon atoms, each of which is optionally substituted by hydroxyl, fluorine, chlorine, bromine or by straight-chain or branched alkoxy, acyl, alkylthio or alkoxycarbonyl having in each case up to 6 carbon atoms, or by phenyl, which can in turn by substituted by fluorine, chlorine or bromine, or represents phenyl, which is optionally substituted by carboxyl, fluorine, chlorine, bromine, iodine, cyano, trifluoromethyl, formyl, nitro or straight-chain or branched alkoxy, alkoxycarbonyl, alkylthio or acyl having in each case up to 4 carbon atoms, or by straight-chain or branched alkyl having up to 4 carbon atoms, or represents a radical of the formula —NR$^{20}$R$^{21}$, —OR$^{22}$ or —S(O)$_c$—R$^{23}$, wherein R$^{20}$ denotes cyclopropyl, cyclopentyl, cyclohexyl, phenyl, straight-chain or branched acyl having up to 4 carbon atoms or straight-chain or branched alkyl having up to 6 carbon atoms, which is optionally substituted by hydroxyl, straight-chain or branched alkoxy or hydroxy-substituted alkoxy having in each case up to 5 carbon atoms, pyridyl, pyrazinyl, pyrimidyl or by phenyl, which can in turn be substituted by hydroxyl, trifluoromethyl, fluorine, chlorine, bromine, nitro or by straight-chain or branched alkoxy having up to 3 carbon atoms, or alkyl is optionally substituted by a radical of the formula —NR$^{24}$R$^{25}$ or

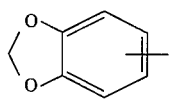

wherein

R$^{24}$ and R$^{25}$ are identical or different and denote hydrogen or straight-chain or branched alkyl having up to 3 carbon atoms, or R$^{20}$ denotes a radical of the formula

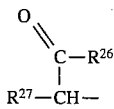

wherein

R$^{26}$ denotes hydroxyl, straight-chain or branched alkoxy having up to 3 carbon atoms or a radical of the formula —NR$^{28}$R$^{29}$, wherein R$^{28}$ and R$^{29}$ are identical or different and denote hydrogen, straight-chain or branched alkyl having up to 3 carbon atoms, cyclopropyl, cyclopentyl, cyclohexyl or phenyl, R$^{27}$ denotes hydrogen or straight-chain or branched alkyl having up to 5 carbon atoms, which is optionally substituted by phenyl, or R$^{20}$ denotes a radical of the formula

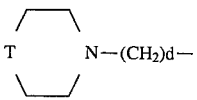

wherein d denotes the number 0, 1, 2 or 3,

T denotes an oxygen atom or a group of the formula —CH$_2$ or —NR$^{30}$, wherein R$^{30}$ denotes hydrogen, phenyl or straight-chain or branched alkyl having up to 4 carbon atoms, which is optionally substituted by hydroxyl, and R$^{21}$ has the abovementioned meaning of R$^{20}$ and is identical to or different from this, or denotes hydrogen, R$^{22}$ denotes straight-chain or branched alkyl having up to 6 carbon atoms, which is optionally substituted by straight-chain or branched alkoxy or hydroxy- or alkoxy-substituted alkoxy having in each case up to 5 carbon atoms, cyclopropyl, cyclopentyl, cyclohexyl, pyridyl, pyrimidyl, pyrazinyl or quinolyl, each of which can in turn be substituted by nitro, trifluoromethyl, fluorine, chlorine, bromine, cyano, hydroxyl or by straight-chain or branched alkyl, alkoxy or acyl having in each case up to 4 carbon atoms, or R$^{22}$ denotes a radical of the formula

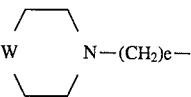

wherein e has the abovementioned meaning of d and is identical to or different from this, W has the abovementioned meaning of T and is identical to or different from this, or $R^{22}$ denotes phenyl or pyridyl, c denotes the number 0, 1 or 2, $R^{23}$ denotes straight-chain or branched alkyl or alkenyl having in each case up to 14 carbon atoms, which is optionally substituted by straight-chain or branched alkoxycarbonyl having up to 4 carbon atoms or by phenyl, thienyl, furyl, pyrrolyl, imidazolyl, pyridyl, pyrazinyl, pyrimidyl or pyridazinyl, or denotes phenyl, thienyl, furyl, pyrrolyl, imidazolyl, pyridinyl, pyrazinyl, pyrimidyl or pyridazinyl, and wherein the abovementioned cyclic radicals are optionally substituted up to twice in an identical or different manner by carboxyl, fluorine, chlorine, bromine, iodine, cyano, trifluoromethyl, formyl, nitro, straight-chain or branched alkoxy, alkoxycarbonyl, alkylthio or acyl having in each case up to 4 carbon atoms or by straight-chain or branched alkyl having up to 4 carbon atoms, or $R^2$ represents morpholinyl, or represents a radical of the formula

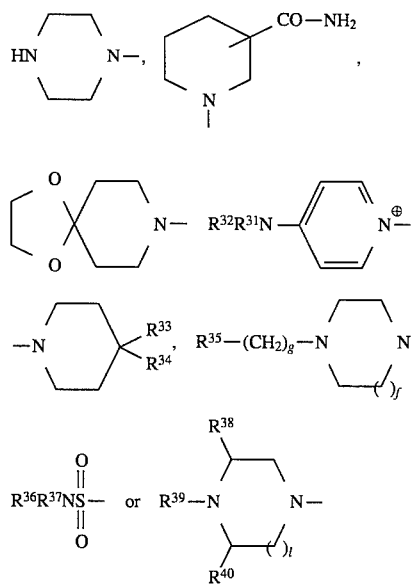

wherein $R^{31}$ and $R^{32}$ have the abovementioned meaning of $R^{24}$ and $R^{25}$ and are identical to or different from these, $R^{33}$ and $R^{34}$ together form a radical of the formula =O or $R^{33}$ and $R^{34}$ are identical or different and denote hydrogen, hydroxyl or straight-chain or branched alkyl having up to 4 carbon atoms, which is optionally substituted by a group of the formula —$NR^{41}R^{42}$, wherein $R^{41}$ and $R^{42}$ have the abovementioned meaning of $R^{24}$ and $R^{25}$ and are identical to or different from these, f denotes the number 0 or 1, g denotes the number 0, 1, 2, 3 or 4, $R^{35}$ denotes phenyl, pyridyl, pyrimidyl, pyrazinyl or quinolyl, each of which can in turn be substituted up to twice in an identical or different manner by nitro, cyano, hydroxyl, phenyl, fluorine, chlorine, bromine, trifluoromethyl or by straight-chain or branched alkyl, alkoxy or acyl having in each case up to 4 carbon atoms, or $R^{35}$ denotes morpholinyl, hydroxyl, straight-chain or branched alkoxy having up to 4 carbon atoms or a radical of the formula

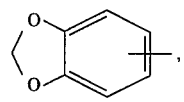

—$NR^{43}R^{44}$ or —CO—$R^{45}$, wherein $R^{43}$ and $R^{44}$ are identical or different and have the abovementioned meaning of $R^{24}$ and $R^{25}$, $R^{45}$ denotes morpholinyl, hydroxyl or straight-chain or branched alkoxy having up to 5 carbon atoms, $R^{36}$ and $R^{37}$ are identical or different and denote hydrogen, phenyl or straight-chain or branched alkyl having up to 4 carbon atoms or benzyl, $R^{38}$, $R^{39}$ and $R^{40}$ are identical or different and have the abovementioned meaning of $R^{30}$ and are identical to or different from this, l denotes the number 1 or 2, and salts thereof.

3. Compounds according to claim 1, in which

A represents an oxygen atom, or represents a radical of the formula —$S(O)_a$—, wherein a denotes the number 0 or 2, $R^1$ represents azido, or represents a group of the formula —$OSO_2R^3$ or —$NR^4R^5$, wherein $R^3$ denotes methyl, ethyl, phenyl or tolyl, $R^4$ and $R^5$ are identical or different and denote cyclopropyl, cyclopentyl, cyclohexyl, hydrogen, phenyl or straight-chain or branched alkyl having up to 5 carbon atoms, or $R^4$ or $R^5$ denote a group of the formula —CO—$R^6$, wherein $R^5$ denotes cyclopropyl, cyclopentyl, cyclohexyl or straight-chain or branched alkyl or alkoxy having in each case up to 4 carbon atoms, hydrogen or phenyl, G, L and M are identical or different and represent hydrogen, carboxyl, fluorine, chlorine, bromine, iodine, cyano, formyl or nitro, or represent straight-chain or branched alkyl having up to 3 carbon atoms, and/or represent a group of the formula —$NR^{7'}R^{8'}$, wherein $R^{7'}$ and $R^{8'}$ are identical or different and denote hydrogen or methyl, $R^2$ represents hydrogen, formyl, carboxyl or straight-chain or branched alkoxycarbonyl having up to 3 carbon atoms, or represents straight-chain or branched alkyl or alkenyl having in each case up to 4 carbon atoms, each of which is optionally substituted by hydroxyl, fluorine, chlorine, bromine or by straight-chain or branched alkoxy, acyl, alkylthio or alkoxycarbonyl having in each case up to 3 carbon atoms or by phenyl, which can in turn be substituted by chlorine, or represents phenyl, which is optionally substituted by carboxyl, fluorine, chlorine, bromine, iodine, cyano, formyl, trifluoromethyl, nitro, straight-chain or branched alkoxy, alkoxycarbonyl or acyl having in each case up to 3 carbon atoms or by straight-chain or branched alkyl having up to 3 carbon atoms, or represents a radical of the formula —$NR^{20}R^{21}$, —$OR^{22}$ or —$S(O)_c$—$R^{23}$, wherein $R^{20}$ denotes cyclopropyl, cyclopentyl, cyclohexyl, phenyl, straight-chain or branched acyl having up to 3 carbon atoms, or straight-chain or branched alkyl having up to 4 carbon atoms, which is optionally substituted by hydroxyl, straight-chain or branched alkoxy or hydroxy-substituted alkoxy having in each case up to 3 carbon atoms, pyridyl, pyrimidyl or pyrazinyl, or by phenyl, which can in turn be substituted by hydroxyl, trifluoromethyl, fluorine, chlorine, bromine, nitro, methoxy or ethoxy, or alkyl is optionally substituted by a radical of the formula —NR$^{24}$R$^{25}$ or

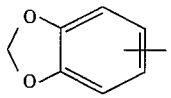

wherein

R$^{24}$ and R$^{28}$ are identical or different and denote hydrogen, methyl or ethyl, or

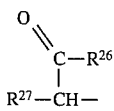

R$^{20}$ denotes a radical of the formula wherein

R$^{26}$ denotes hydroxyl, methoxy, ethoxy or a radical of the formula —NR$^{28}$R$^{29}$, wherein R$^{28}$ and R$^{29}$ are identical or different and denote hydrogen, methyl, ethyl, cyclopropyl or phenyl, R$^{27}$ denotes hydrogen or straight-chain or branched alkyl having up to 3 carbon atoms, which is optionally substituted by phenyl, or

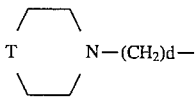

R$^{20}$ denotes a radical of the formula wherein d denotes the number 0, 1, 2 or 3, T denotes an oxygen atom or a group of the formula —CH$_2$ or —NR$^{30}$, wherein R$^{30}$ denotes hydrogen or straight-chain or branched alkyl having up to 3 carbon atoms, which is optionally substituted by hydroxyl, and R$^{21}$ has the abovementioned meaning of R$^{20}$ and is identical to or different from this, or denotes hydrogen, R$^{22}$ denotes straight-chain or branched alkyl having up to 4 carbon atoms, which is optionally substituted by straight-chain or branched alkoxy or hydroxy- or alkoxy-substituted alkoxy having in each case up to 4 carbon atoms, cyclopropyl, cyclopentyl, cyclohexyl, pyridyl, pyrazinyl or pyrimidyl, which can in turn be substituted by nitro, trifluoromethyl, fluorine, chlorine, bromine, cyano, hydroxyl or by straight-chain or branched alkyl, alkoxy or acyl having in each case up to 3 carbon atoms, or R$^{22}$ denotes a radical of the formula

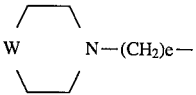

wherein e has the abovementioned meaning of d and is identical to or different from this, W has the abovementioned meaning of T and is identical to or different from this, or R$^{22}$ denotes phenyl or pyridyl, c denotes the number 0, 1 or 2, R$^{23}$ denotes straight-chain or branched alkyl or alkenyl having up to 13 carbon atoms, which is optionally substituted by straight-chain or branched alkoxycarbonyl having up to 3 carbon atoms or phenyl or by thienyl, pyridyl, pyrazinyl or pyrimidyl, or denotes phenyl, thienyl, pyridyl, pyrazinyl or pyrimidyl, and in which the abovementioned cyclic radicals are optionally substituted by carboxyl, fluorine, chlorine, bromine, iodine, cyano, formyl, trifluoromethyl, nitro, straight-chain or branched alkoxy, alkoxycarbonyl or acyl having in each case up to 4 carbon atoms or by straight chain or branched alkyl having up to 4 carbon atoms, or R$^2$ represents morpholinyl, or represents a radical of the formula

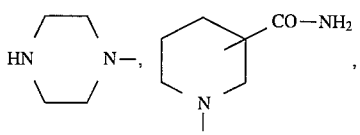

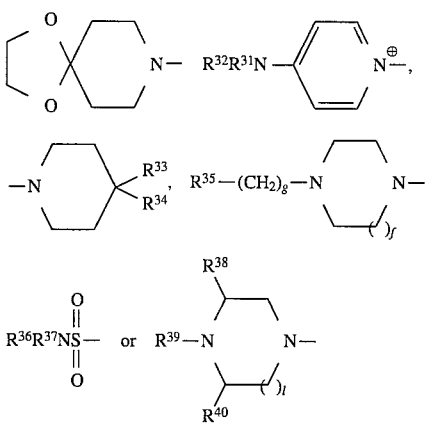

wherein

R$^{31}$ and R$^{32}$ have the abovementioned meaning of R$^{24}$ and R$^{25}$ and are identical to or different from these, R$^{33}$ and R$^{34}$ together form a radical of the formula =O or R$^{33}$ and R$^{34}$ are identical or different and denote hydrogen, hydroxyl or straight-chain or branched alkyl having up to 3 carbon atoms, which is optionally substituted by a group of the formula —NR$^{41}$R$^{42}$, wherein R$^{41}$ and R$^{42}$ have the abovementioned meaning of R$^{24}$ and R$^{25}$ and are identical to or different from these, f denotes the number 0 or 1, g denotes the number 0, 1, 2 or 3, R$^{35}$ denotes phenyl, pyridyl, pyrazinyl or pyrimidyl, each of which can in turn by substituted by nitro, cyano, hydroxyl, phenyl, fluorine, chlorine, bromine, trifluoromethyl or by straight-chain or branched alkyl, alkoxy or acyl having in each case up to 3 carbon atoms, or R$^{35}$ denotes morpholinyl, hydroxyl, straight-chain or branched alkoxy having up to 3 carbon atoms or a radical of the formula

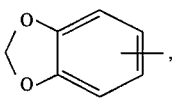

—NR$^{43}$R$^{44}$ or —CO—R$^{45}$, wherein

R$^{43}$ and R$^{44}$ are identical or different and have the abovementioned meaning of R$^{24}$ and R$^{25}$, R$^{45}$ denotes morpholinyl, hydroxyl or straight-chain or branched alkoxy having up to 4 carbon atoms, R$^{36}$ and R$^{37}$ are identical or different and denote hydrogen, phenyl or straight-chain or branched alkyl having up to 3 carbon atoms or benzyl, R$^{38}$, R$^{39}$ and R$^{40}$ are identical or different and have the abovementioned meaning of R$^{30}$ and are identical to or different from this, l denotes the number 1 or 2, and salts thereof.

4. Compounds according to claim 1, in which

G, L and M represent hydrogen and the oxazolidinone radical is bonded to the phenyl ring in positions 5 or 6.

5. A pharmaceutical composition which comprises a compound according to claim 1 and an inert carrier.

6. A method for treating bacterial infections to a human or animal in need thereof which comprises administering a compound according to claim 1 to said animal or human.

* * * * *

UNITED STATES PATENT AND TRADEMARK OFFICE
CERTIFICATE OF CORRECTION

PATENT NO. : 5,529,998
DATED : June 25, 1996
INVENTOR(S) : Habich, et al.

It is certified that error appears in the above-indentified patent and that said Letters Patent is hereby corrected as shown below:

| | |
|---|---|
| Col. 75, line 33 | Delete " rum " and substitute -- turn -- |
| Col. 76, line 65 | Delete " different from this " (second occurrence) |
| Col. 77, line 65 | Delete " ting " and substitute -- ring - |
| Col. 79, line 42 | Delete " by " (second occurrence) and substitute -- be -- |

Signed and Sealed this

Fourth Day of March, 1997

Attest:

BRUCE LEHMAN

*Attesting Officer*  *Commissioner of Patents and Trademarks*